US012693257B2

(12) United States Patent
Somasundaram et al.

(10) Patent No.: US 12,693,257 B2
(45) Date of Patent: Jul. 28, 2026

(54) DNA-BASED ASSAYS

(71) Applicant: AUBURN UNIVERSITY, Auburn, AL (US)

(72) Inventors: Subramaniam Somasundaram, Auburn, AL (US); Anup Singh, Media, PA (US); Eshwar Inapuri, Novi, MI (US)

(73) Assignee: AUBURN UNIVERSITY, Auburn, AL (US)

( * ) Notice: Subject to any disclaimer, the term of this patent is extended or adjusted under 35 U.S.C. 154(b) by 293 days.

(21) Appl. No.: 18/247,196

(22) PCT Filed: Sep. 29, 2021

(86) PCT No.: PCT/US2021/052560
§ 371 (c)(1),
(2) Date: Mar. 29, 2023

(87) PCT Pub. No.: WO2022/072432
PCT Pub. Date: Apr. 7, 2022

(65) Prior Publication Data

US 2023/0375496 A1 Nov. 23, 2023

Related U.S. Application Data

(60) Provisional application No. 63/084,665, filed on Sep. 29, 2020.

(51) Int. Cl.
*G01N 27/327* (2006.01)
*C12Q 1/6804* (2018.01)
*C12Q 1/6825* (2018.01)

(52) U.S. Cl.
CPC ....... *G01N 27/3277* (2013.01); *C12Q 1/6804* (2013.01); *C12Q 1/6825* (2013.01)

(58) Field of Classification Search
None
See application file for complete search history.

(56) References Cited

U.S. PATENT DOCUMENTS 5,635,352 A 6/1997 Urdea et al.
5,698,448 A 12/1997 Soldin
(Continued)

FOREIGN PATENT DOCUMENTS

EP 1198591 A1 4/2002
EP 1806414 A2 7/2007
(Continued)

OTHER PUBLICATIONS

Somasundaram, et al., "A Nucleic Acid Nanostructure Built through On-Electrode Ligation for Electrochemical Detection of a Broad Range of Analytes", Journal of the American Chemical Society, 141(29): p. 11721-11726, Jun. 30, 2019.*
(Continued)

*Primary Examiner* — J. Christopher Ball
(74) *Attorney, Agent, or Firm* — Barnes & Thornburg LLP

(57) ABSTRACT

Described herein DNA-based assays that include nanostructures providing a simple, highly sensitive method for small molecule, biologic and peptide measurements that are optimized for use in a commercial, point-of-care diagnostic settings and systems. These DNA-based assays may include a combination of multiple redox molecules (e.g., methylene blue) such as between 3-8 redox molecules, and a spacer of between about 2 A and 20 A (and in particular between 3 A and 8 A), that results in an assay that has significantly greater signal and greater sensitivity as compared to prior DNA-based assays.

14 Claims, 3 Drawing Sheets

Specification includes a Sequence Listing.

(56) References Cited

U.S. PATENT DOCUMENTS

| | | | |
|---|---|---|---|
| 6,264,825 | B1 | 7/2001 | Blackburn et al. |
| 6,350,580 | B1 | 2/2002 | Sorge |
| 6,361,944 | B1 | 3/2002 | Mirkin et al. |
| 6,506,564 | B1 | 1/2003 | Mirkin et al. |
| 6,750,016 | B2 | 6/2004 | Mirkin et al. |
| 6,767,702 | B2 | 7/2004 | Mirkin et al. |
| 6,773,884 | B2 | 8/2004 | Mirkin et al. |
| 6,984,491 | B2 | 1/2006 | Mirkin et al. |
| 7,005,265 | B1 | 2/2006 | Fan et al. |
| 7,169,556 | B2 | 1/2007 | Park et al. |
| 7,291,457 | B2 | 11/2007 | Miller et al. |
| 7,803,542 | B2 | 9/2010 | Xiao et al. |
| 7,807,352 | B2 | 10/2010 | Rabbani et al. |
| 8,003,374 | B2 | 8/2011 | Heeger et al. |
| 9,335,292 | B2 | 5/2016 | Hu et al. |
| 10,852,274 | B2 | 12/2020 | Easley et al. |
| 11,505,799 | B2 | 11/2022 | Inapuri et al. |
| 11,560,565 | B2 | 1/2023 | Easley et al. |
| 2001/0024788 | A1 | 9/2001 | Hashimoto |
| 2002/0006617 | A1 | 1/2002 | Fan et al. |
| 2002/0012943 | A1 | 1/2002 | Fowlkes et al. |
| 2002/0172953 | A1 | 11/2002 | Mirkin et al. |
| 2003/0022150 | A1 | 1/2003 | Sampson et al. |
| 2003/0077642 | A1 | 4/2003 | Fritsch et al. |
| 2003/0108922 | A1 | 6/2003 | Fritsch et al. |
| 2004/0106190 | A1 | 6/2004 | Yang et al. |
| 2004/0191801 | A1 | 9/2004 | Heeger et al. |
| 2005/0096288 | A1 | 5/2005 | Guevara |
| 2005/0112605 | A1 | 5/2005 | Heeger et al. |
| 2005/0164286 | A1 | 7/2005 | Ouchi et al. |
| 2005/0202449 | A1 | 9/2005 | Getts et al. |
| 2006/0228703 | A1 | 10/2006 | Hartwich et al. |
| 2006/0234253 | A1 | 10/2006 | Hasui et al. |
| 2007/0084721 | A1 | 4/2007 | Hsung et al. |
| 2007/0236224 | A1 | 10/2007 | Augustyniak et al. |
| 2008/0076139 | A1 | 3/2008 | Singh |
| 2008/0302666 | A1 | 12/2008 | Benner et al. |
| 2009/0042735 | A1 | 2/2009 | Blair et al. |
| 2009/0305264 | A1 | 12/2009 | West et al. |
| 2010/0035248 | A1 | 2/2010 | Levicky et al. |
| 2010/0075319 | A1 | 3/2010 | Lohse |
| 2010/0248231 | A1 | 9/2010 | Wei et al. |
| 2010/0297654 | A1 | 11/2010 | Heyduk |
| 2011/0053788 | A1 | 3/2011 | Bamdad et al. |
| 2011/0143955 | A1 | 6/2011 | Weiner |
| 2012/0021426 | A1 | 1/2012 | Takoh et al. |
| 2012/0028242 | A1 | 2/2012 | Heyduk et al. |
| 2015/0050645 | A1 | 2/2015 | Takoh |
| 2019/0250120 | A1 | 8/2019 | Korri-Youssoufi et al. |
| 2021/0055260 | A1 | 2/2021 | Easley et al. |
| 2023/0042710 | A1 | 2/2023 | Ford et al. |

FOREIGN PATENT DOCUMENTS

| | | | |
|---|---|---|---|
| WO | WO01/040511 | A2 | 6/2001 |
| WO | WO01/051665 | A2 | 7/2001 |
| WO | WO01/073123 | A2 | 10/2001 |
| WO | WO02/018643 | A2 | 3/2002 |
| WO | WO02/046472 | A2 | 6/2002 |
| WO | WO03/035829 | A2 | 5/2003 |
| WO | WO2004/023128 | A1 | 3/2004 |
| WO | WO2006/096185 | A2 | 9/2006 |
| WO | WO2008/001376 | A2 | 1/2008 |
| WO | WO2008/054517 | A2 | 5/2008 |
| WO | WO2018/111745 | A1 | 6/2008 |
| WO | WO2011/017382 | A2 | 2/2011 |
| WO | WO2011/050069 | A1 | 4/2011 |
| WO | WO2011/161420 | A2 | 12/2011 |
| WO | WO2015/150482 | A1 | 10/2015 |
| WO | WO2017/192737 | A1 | 11/2017 |
| WO | WO2018/011412 | A1 | 1/2018 |
| WO | WO2021/016615 | A1 | 1/2021 |
| WO | WO2021/138621 | A1 | 7/2021 |
| WO | WO2022/072432 | A1 | 4/2022 |

OTHER PUBLICATIONS

Supplementary European Search Report prepared for Application No. 21876356.3, mailed Sep. 30, 2024.

Arroyo-Curras et al.; Real-time measurement of small molecules directly in awake, ambulatory animals; Proceedings of the National Academy of Sciences; 114(4); pp. 645-650; Jan. 24, 2017.

Baker et al.; An electronic aptamer-based small-molecule sensor for the rapid, label-free detection in adulterated samples and biological fluids; Journal of the American Chenical Society; 128(10); pp. 3138-3139; Mar. 2006.

Bonham et al.; Detection of IP-10 protein marker in undiluted blood serum via an electrochemical e-dna scaffold sensor; Analyst: 138(19); pp. 5580-5583; 9 pages (Author Manuscript); Oct. 7, 2013.

Campos et al.; Amperometric detection of lactose using ?- galactosidase immobilized in layer films; ACS Applied Materials and Interfaces; 6(14); pp. 11657-11664; 8 pages (Author Manuscript); Jul. 11, 2014.

Carrillo et al.; The multiple sequence aligment problem in biology; SIAM Journal on Applied Mathematics; 48(5); pp. 1073-1082; Oct. 1988.

Cash et al.; An electrochemical sensor for the detection of protein-small molecule interactions directly in serum and other complex matrices; Journal of the American Chemical Society: 131(20); pp. 6955-6957; May 4, 2009.

De Crozals et al.; Methylene blue phosphoramidite for DNA labelling; ChemCommun; vol. 51(2); pp. 4458-4461; Mar. 14, 2014.

Denman et al.; Continuous differential monitoring of the spend dialysate glucose level: clinical evaluation; Sensors and Actuators B: Chemical; 44 (1-3); pp. 304-308; Oct. 1, 1997.

Deng et al.; Sensitive bifunctional aptamer-based electrochemical biosensor for small molecules and protein; Analytical Chemistry; 81(24); pp. 9972-9978; Nov. 19, 2009.

Dirks et al.; A partition function algorithm for nucleic secondary structure including pseudoknots; Journal of Computational Chemisrty; 24(10); pp. 1664-1677; Oct. 2003.

Dirks et al.; An algorithm for computing nucleic acid base-pairing proabilities including pseudoknots; Journal of Computational Chemisrty: 25(10); pp. 1295-1304; Jul. 30, 2004.

Dirks et al.; Paradigms for computational nucleic acid design; Nucleic Acid Research; 32(4); pp. 1392-1403; Feb. 27, 2004.

Dirks et al.; Thermodynamic analysis of interacting nucleic acid strands; SIAM Rev .; 49(1); pp. 65-88; (the year of publication is sufficiently earlier than the effective U.S. filing date and any foreign priority date so that the particular month of publication is not in issue) 2007.

Dryden et al.; Dstat: A versatile, open-source potentiostat for electroanalysis and integration; PLOS One; DOI: 10.1371/journal.pone.0140349; 17 pages; Oct. 28, 2015.

Du et al.; Multifunctional label-free electrochemical biosensor based on an integrated aptamer; Analytical Chemistry; 80(13); pp. 5110-5117; Jun. 4, 2008.

Fan et al.; A Competitor-switched electrochemical sensor for detection of dna; Chin. J. Chem.; 28; pp. 1978-1982; (the year of publication is sufficiently earlier than the effective U.S. filing date and any foreign priority date so that the particular month of publication is not in issue) 2010.

Fan et al.; Electrochemical interrogation of conformational changes as a reagentless method for the sequence-specific detection of dna; Proceedings of the National Academy of Scieones: 100(16); pp. 9134-9137; Aug. 5, 2003.

Ferapontova et al.; An rna aptamer-based electrochemical biosensor for detection of theophylline in serum; Journal of the American Chemical Society; 130(13); pp. 4256-4258; Apr. 2, 2008.

Ferguson et al.; Real-time, aptamer-based tracking of circulating therapeutic agents in living animals; Science Translational Medicine; 5(213); pp. 213ra165, 11 pages; Nov. 27, 2013.

Garcia-Gonzalez et al.; Methylene blue covalently attached to single stranded DNA as electroactive label for potential bioassays; Sensors and Actuators B: Chemical; vol. 191; pp. 784-790; Feb. 1, 2014.

Hirsch et al.; Easily reversible desthiobiotin binding to streptavidin, avidin, and other biotin-binding proteins: uses for protein labeling,

(56) References Cited

OTHER PUBLICATIONS detection, and isolation; Analytical biochemistry; 308(2); pp. 343-357.
Hu et al.; A reusable electrochemical proximity assay for highly selective, real-time protein quantitation in biological matrices; Journal of the American Chemical Society: 136(23); pp. 8467-8474; May 30, 2014.
Huang et al.; Random walk on a leash: a simple single-molecule diffusion model for surface-tethered redox molecules with flexible linkers; Journal of the American Chemical Society: 135(34); pp. 12808-12817; Aug. 20, 2013.
Idili et al.; Folding-upon-binding and signal-on electrochemical dna sensor with high affinity and specificity: Analytical Chemistry; 86(18); pp. 9013-9019; Jul. 3, 2014.
Jakubowska; Signal processing in electrochemistry; Electroanalysis; 23(3); pp. 553-572; Mar. 2011.
Jeyarajah et al.; Lipoprotein particle analysis by nuclaer magnetic resoance spectroscopy; Clinics in Laboratory Medicine; 26(4); pp. 847-870; Dec. 2006.
Kaess et al.; The lipoprotein sub-fraction profile hertability and indentification of quantitative trait loci; Journal of Lipid Research; 49(4); pp. 715-723; Apr. 2008.
Kang et al.; Comparing the properties of electrochemical-based dna sensors employing different redox tags, Analytical Chemistry; 81(21); pp. 9109-9113; 12 pages (Author Manuscript); Oct. 7, 2009.
Kang et al.; Expanding the scope of protein-detecting electrchemical dna "scaffold" sensors; ACS Sensors; 3(7); pp. 1271-1275; 12 pages (Author Manuscript); Jun. 2018.
Kick et al.; EGNAS: an exhaustive dna sequence design algorithm; BMC Bioinformatics; 13(1); pp. 138; 17 pages; http://www.biomedcentral.com/1471-2105/13/138; Dec. 2012.
Labib et al.; Electrochemical methods for the analysis of clinically relevant biomolecules; Chemical Reviews; 116(16); pp. 9001-9090; Jul. 18, 2016.
Lee et al.; Fabricating RNA Microarrays with RNA? DNA Surface Ligation Chemistry. Analytical chemistry; 77(23); pp. 7832-7837; Dec. 1, 2005.
Li et al.; A simple assay to amplify the electrochemical signal by the aptamer based biosensor modified with CdS hollow nanospheres; Biosensors and Bioelectronics; 26(8); pp. 3531-3535; Apr. 15, 2011.
Li et al.; Target-responsive structural switching for nucleic acid-based sensors, Accounts of Chemical Research; 43(5); pp. 631-641; Mar. 11, 2010.
Lin et al.; Label-free aptamer-based electrochemical impedance biosensor for 17? estradiol; Analyst; 137(4); pp. 819-822; Feb. 2012.
Liu et al.; Aptamer-based electrochemical biosensors for interferon gamma detection; Analytical Chemistry; 82(19); pp. 8131-8136; Sep. 3, 2010.
Lu et al.; Aptamer-based electrochemical sensors that are not based on the target binding-induced conformational change of aptamers; Analyst; 133(9); pp. 1256-1260; Sep. 2008.
Lubin et al.; Effects of probe length, probe geometry, and redox-tag placement on the performance of the electtrochemical e-dna sensor; Analytical Chemistry; 81(6); pp. 2150-2158; Feb. 12, 2009.
Mage; Closed-loop control of circulating drug levels in live animals; Nature Biomedical Engineering; 1(5); DOI: 10.1038/s415551-017-0070, 10 pages; May 2017.
Mahshid et al.; A highly selective electrochemical dan-based sensor that employs steric hindrance effects to detect proteins directly in whole blood; Journal of the American Chemical Society; 137(50); pp. 15596-15599; Sep. 24, 2015.
Mahshid et al.; Biomolecular steric hindrance effects are enhanced on nanostructured microelectrodes; Analytical Chemistry; 89(18); pp. 9751-9757; Sep. 5, 2017.
Mahshid et al.; Electrochemical dna-based immunoassay that employs steric hindrance to detect small molecules directly in whole blood; AACS Sensors; 2(6); pp. 718-723; May 25, 2017.
Needleman et al.; A general method applicable to the search for similarities in the amino scid sequence of two proteins; Journal of Molecular Biology; 48(3); pp. 443-453; Mar. 1970.
Sacks et al.; Clinical review 163: cardiovascular endocrinology: low-density lipoprotein size and cardovascular disease: a reappraisal; The Journal of Clinical Endocrinology and Metabolism; 88(10); pp. 4525-4532; Oct. 2003.
Schoukroun-Barnes et al.; Reagentless, structure-switching, electrochemical aptamer-based sensors; Annual Review of Analtyical Chemistry; 9(1); pp. 163-181; 23 pages (Author Manuscript) Jun. 2016.
Sheth et al.; Decapping and decay of messenger RNA occur in cytoplasmic processing bodies; Science; 300; pp. 805-808; May 2003.
Sigma-Aldrich; Self-assembled monolayers: advantages of pure alkanethiols; 4 pages retrieved from the internet (https://www.sigmaaldrich.com/technical-documents/articles/material-matters/self-assembled-monolayers.html) on Dec. 10, 2019.
Silva et al.; Gold electrode modified by self-assembled monolayers of thiolis to determine dna sequences hybridization; Journal of Chemical Sciences; 122(6); pp. 911917; Nov. 2010.
Somasundaram et al.; A nucleic acid nanostructure built through on-electrode ligation for electrochemical detection of a board range of analytes; Journal of the American Chemical Society; 141(29); pp. 11721-11726; 14 pages; (Author Manuscript); Jun. 2019.
Somasundaram et al.; Understanding signal and background in a thermally resolved, single-branched dna assay using sqaure wave voltammetry; Analytical Chemistry; 90(50); pp. 3584-3591; 18 pages (Author Manuscript); Jan. 31, 2018.
Suna et al.; 1H NMR metabolomics of plasma lipoprotein subclasses: elucidation of metabolic clustering by self-organizing maps; NMR in Biomedicine; 20(7); pp. 658-672; Nov. 2007.
Tong et al.; Simply amplified electrochemical aptasensor of ochratoxin a based on exonuclease-catalyzed target; Biosensors and Bioelectronics; 29(1); pp. 97-101; Nov. 15, 2011.
Turner; Biosensors: sense and sensibility; Chemical Society Reviews; 42(8); pp. 3184-3196; (the year of publication is sufficiently earlier than the effective U.S. filing date and any foreign priority date so that the particular month of publication is not in issue) 2013.
Wang et al.; A sensitive ligase-based atp electrochemical assay using molecular beacon-like dna; Biosensor and Bioelectronics; 25(9); pp. 2101-2106; May 2010.
White et al.; Exploiting binding changes in probe flexibility for the optimization of electrochemical biosensors; Analytical Chemistry; 82(1); pp. 73-76; 10 pages (Author Manuscript); Dec. 10, 2009.
Wolfe et al.; Constrained multistate sequence design for nucleic acid reaction pathway engineering; Journal of American Chemical Society: 139(8); pp. 3134-3144; Feb. 13, 2017.
Wolfe et al.; Sequence design for a test tube of interacting nucleic acid strands; ACS Synthetic Biology; 4(10); pp. 1086-1100; Oct. 20, 2014.
Wu et al.; Reusable electrochemical sensing platform for highly sensitive detection of small molecules based on structure-switching signal aptamers; Analytical Chemistry; 79(7); pp. 2933-2939; Apr. 2007.
Xiao et al.; A reagentless signal-on architecture for electronic, aptamer-based sensors via target-induced strand displacement; Journal of the American Chemical Society; 127(51); pp. 17990-17991; (Author Manuscript); Dec. 28, 2005.
Xiao et al.; Preparation of electrode-immobilized, redox-modified oligonucleotides for electrochemical dna and aptamer-based sensing; Nature Protocols; 2(11); pp. 2875-2880; Nov. 2007.
Yeung et al.; Electrochemical real-time polymerase chain reaction; Journal of the American Chemical Society; 128(41); pp. 13374-13375; Oct. 18, 2006.
Zadeh et al.; Nucleic acid sequence design via efficient ensemble defect optimization; Journal of Computational Chemistry; 32(3); pp. 439-452; Feb. 2011.
Zadeh et al.; NUPACK: analysis and design of nucleic acid systems; Journal of computational Chemistry; 32(1); pp. 170-173; Jan. 15, 2011.
Zhang et al.; Electrochemical aptasensor based on proximity-dependent surface hybridization assay for protein detection;

(56) References Cited

OTHER PUBLICATIONS

Electroanalysis: An International Journal Devoted to Fundamental and Practical Aspects of Electroanalysis; 21(11); pp. 1327-1333; Jun. 2009.
Zhang et al.; Electrochemical aptasensor based on proximity-dependent surface hybridization assay for single-step, reusable, sensitive protein detection; Journal of the American Chemical Society; 129(50); pp. 15448-15449; Published on line Nov. 22, 2007.
Zhao et al.; A label-free electrochemilumescent sensor for atp detection based on atp-dependent ligation; Talanta; 154; pp. 492-497; Jul. 2016.
Zhou et al.; Steric hindrance assay for secreted factors in stem cell culture; ACS Sensors; 2(4); pp. 495-500; Apr. 17, 2017.
Zymek et al.; The role of platelet-derived growth factor signal in healing mycardial infarcts; Journal of the American college of Cardiology; 48(11); pp. 2315-2323; Dec. 5, 2006.
Somasundaram et al.; U.S. Appl. No. 17/616,338 entitled "Assay method for point of care quantification of an immunophilin-binding immunosuppressant drug," filed Dec. 3, 2021.
Easley et al.; U.S. Appl. No. 18/158,466 entitled "Electrochemical detection nanostructure, systems, and uses thereof," filed Jan. 23, 2023.

* cited by examiner

SEQUENCE LISTING

```
<160> NUMBER OF SEQ ID NOS: 13

<210> SEQ ID NO 1
<211> LENGTH: 37
<212> TYPE: DNA
<213> ORGANISM: Artificial Sequence
<220> FEATURE:
<223> OTHER INFORMATION: 4A length tether (5' end is modified by a
      Phosphate grp; 3' end is modified by ThioMC3-D grp)

<400> SEQUENCE: 1

ctgtgcaaga actcacagcc tcacctcttc ctaaaaa                          37


<210> SEQ ID NO 2
<211> LENGTH: 39
<212> TYPE: DNA
<213> ORGANISM: Artificial Sequence
<220> FEATURE:
<223> OTHER INFORMATION: 6A length tether (5' end is modified by a
      Phosphate grp; 3' end is modified by ThioMC3-D grp)

<400> SEQUENCE: 2

ctgtgcaaga actcacagcc tcacctcttc ctaaaaaaa                        39


<210> SEQ ID NO 3
<211> LENGTH: 41
<212> TYPE: DNA
<213> ORGANISM: Artificial Sequence
<220> FEATURE:
<223> OTHER INFORMATION: 8A length tether (5' end is modified by a
      Phosphate grp; 3' end is modified by ThioMC3-D grp)

<400> SEQUENCE: 3

ctgtgcaaga actcacagcc tcacctcttc ctaaaaaaaa a                     41


<210> SEQ ID NO 4
```

<211> LENGTH: 43
<212> TYPE: DNA
<213> ORGANISM: Artificial Sequence
<220> FEATURE:
<223> OTHER INFORMATION: 10A length tether (5' end is modified by a Phosphate grp; 3' end is modified by ThioMC3-D grp)

<400> SEQUENCE: 4
ctgtgcaaga actcacagcc tcacctcttc ctaaaaaaaa aaa 43

<210> SEQ ID NO 5
<211> LENGTH: 47
<212> TYPE: DNA
<213> ORGANISM: Artificial Sequence
<220> FEATURE:
<223> OTHER INFORMATION: Tac-anchor (5' end is modified by a Phosphate grp; Tacrolimus binding anchor region is present between the residues 33-34)

<400> SEQUENCE: 5
gagacactgt gtcgtctccg gttgaagtgg agaaggaaga ggtgagg 47

<210> SEQ ID NO 6
<211> LENGTH: 14
<212> TYPE: DNA
<213> ORGANISM: Artificial Sequence
<220> FEATURE:
<223> OTHER INFORMATION: MB-DNA (5' end is modified by a dTMB grp)

<400> SEQUENCE: 6
ctccacttca accg 14

<210> SEQ ID NO 7
<211> LENGTH: 18
<212> TYPE: DNA
<213> ORGANISM: Artificial Sequence
<220> FEATURE:
<223> OTHER INFORMATION: 5MB-DNA

<400> SEQUENCE: 7
cgacctccac ttcaaccg 18

<210> SEQ ID NO 8
<211> LENGTH: 98
<212> TYPE: DNA
<213> ORGANISM: Artificial Sequence
<220> FEATURE:
<223> OTHER INFORMATION: Full length 4A sensor (5'-3')

<400> SEQUENCE: 8
ctccacttca accggagaca ctgtgtcgtc tccggttgaa gtggagaagg aagaggtgag 60
gctgtgcaag aactcacagc ctcacctctt cctaaaaa 98

<210> SEQ ID NO 9
<211> LENGTH: 100
<212> TYPE: DNA
<213> ORGANISM: Artificial Sequence
<220> FEATURE:
<223> OTHER INFORMATION: Full length 6A sensor (5'-3')

<400> SEQUENCE: 9
ctccacttca accggagaca ctgtgtcgtc tccggttgaa gtggagaagg aagaggtgag 60
gctgtgcaag aactcacagc ctcacctctt cctaaaaaaa 100

<210> SEQ ID NO 10

-continued

```
<211> LENGTH: 102
<212> TYPE: DNA
<213> ORGANISM: Artificial Sequence
<220> FEATURE:
<223> OTHER INFORMATION: Full length 8A sensor (5'-3')

<400> SEQUENCE: 10

ctccacttca accggagaca ctgtgtcgtc tccggttgaa gtggagaagg aagaggtgag     60

gctgtgcaag aactcacagc ctcacctctt cctaaaaaaa aa                       102


<210> SEQ ID NO 11
<211> LENGTH: 104
<212> TYPE: DNA
<213> ORGANISM: Artificial Sequence
<220> FEATURE:
<223> OTHER INFORMATION: Full length 10A sensor (5'-3')

<400> SEQUENCE: 11

ctccacttca accggagaca ctgtgtcgtc tccggttgaa gtggagaagg aagaggtgag     60

gctgtgcaag aactcacagc ctcacctctt cctaaaaaaa aaaa                     104


<210> SEQ ID NO 12
<211> LENGTH: 20
<212> TYPE: DNA
<213> ORGANISM: Artificial Sequence
<220> FEATURE:
<223> OTHER INFORMATION: First Stem portion (5'-3')

<400> SEQUENCE: 12

cacagcctca cctcttccta                                                 20


<210> SEQ ID NO 13
<211> LENGTH: 20
<212> TYPE: DNA
<213> ORGANISM: Artificial Sequence
<220> FEATURE:
<223> OTHER INFORMATION: Second Stem portion (5'-3')

<400> SEQUENCE: 13

gtctccggtt gaagtggaga                                                 20
```

DNA-BASED ASSAYS

CROSS REFERENCE TO RELATED APPLICATIONS

This patent application is a national-stage entry under 35 U.S.C. § 371(b) of PCT International Application No. PCT/US2021/052560, filed Sep. 29, 2021, which claims priority to U.S. provisional patent application No. 63/084,665, titled "METHOD FOR IMPROVING SENSITIVITY FOR DNA-BASED ASSAYS," filed on Sep. 29, 2020, both of which are herein incorporated by reference in their entirety.

INCORPORATION BY REFERENCE

All publications and patent applications mentioned in this specification are herein incorporated by reference in their entirety to the same extent as if each individual publication or patent application was specifically and individually indicated to be incorporated by reference.

REFERENCE TO SEQUENCE LISTING SUBMITTED ELECTRONICALLY

Incorporated by reference in its entirety is a computer-readable nucleotide/amino acid sequence listing submitted concurrently herewith and identified as follows: 3,591 bytes TXT file named "Sequence Listing 55879-414965," created on Feb. 23, 2023.

BACKGROUND

Diagnostics is a critical component of patient care. Among the types of biological targets measured by traditional diagnostics, sensitive detection of small molecule drugs, biologic therapies and peptide biomarkers is important for the movement towards personalized medicine and enabling patient-specific therapy dosing. Current methods for measuring drug levels require a large, laboratory-based clinical chemistry analyzer or an LC-MS system. For certain biologic assays, ELISAs may be available. However, all these methods are slow, cumbersome, and unsuitable for point of care use thereby limiting the ability to use the tests frequently and quickly as required for personalized medicine and precision therapeutic dosing.

Among emerging assay methods, DNA-based methods have shown promise due to the stability of DNA on electrodes and their suitability with electrochemical detection methods which offer great signal stability, simple instrumentation, high sensitivity, ease of calibration and compatibility with miniaturization. Despite their positive attributes, one of the key drawbacks to standard DNA-based assays is the relatively low signals (nA range) elicited from measurements and the current challenges of signal amplification which may require additional, complex conjugations of different types of molecules which are expensive and not commercially viable. What is needed are improved DNA-based electrochemical nanostructure assays that have increased sensitivity, particularly for small molecule, biologic and peptide targets. The DNA-based assays described herein may address this need.

SUMMARY OF THE DISCLOSURE

Described herein DNA-based assays that include nanostructures providing a simple, highly sensitive method for small molecule, biologic and peptide measurements. Despite the promise of the technology, previous versions of such DNA-based assays suffer from low signal which leads to suboptimal probe distance and probe density. The methods and apparatuses (including systems and assays) described herein provide nanostructure-based and general DNA-based assays that can provide significantly higher signals that are optimized for use in a commercial, point-of-care diagnostic settings and systems.

For example, described herein are DNA nanostructure assays that may provide higher signal and improved overall sensitivity than the traditional nanostructure-based assays. In general, these are nucleic acid-based assays for quantification of target analytes (including, but not limited to, small molecules, peptides, proteins, and antibodies, etc.). These assays may be performed on the surface of an electrically conductive base, such as a gold electrode or other substrates, to form a biosensor.

The following patent applications are herein incorporated by reference in their entirety: Ser. No. 16/629,223, titled "APTAMERS FOR MEASURING LIPOPROTEIN LEVELS", field Jul. 6, 2018, PCTUS2020040010, titled "ASSAY METHOD FOR POINT OF CARE QUANTIFICATION OF AN IMMUNOPHILIN-BINDING IMMUNOSUPPRESSANT DRUG," filed Jun. 26, 2020, PCTUS2020043692, titled "MR-PROADM BINDING COMPOSITIONS AND ASSAYS," filed Jul. 27, 2020. These patent applications may be modified and/or improved as described herein.

For example, described herein are DNA-based assays comprising: a continuous DNA molecule comprising a first hairpin structural motif attached to a second hairpin structural motif via a first segment of single stranded DNA; an anchor recognition moiety coupled to the continuous DNA molecule; a signal moiety comprising a plurality of redox molecules, wherein the signal moiety is coupled to the continuous DNA molecule, wherein the signal moiety and the anchor recognition moiety are in effective proximity to each other; and a thiol-DNA spacer segment attached at a first end to an electrically conductive substrate and at a second end to the second hairpin structural motif such that it forms a single stranded tether region at one end of the single continuous DNA molecule extending between 1 A and 20 A, preferably between 6 A and 20 A, more preferably between 8 A and 20 A or 10 A and 20 A.

The methods and apparatuses (e.g., assays, systems, etc.) described herein are configured to have a very high sensitivity even as compared to other DNA-based assays, by taking advantage of the surprising finding that combination of (1) multiple redox molecules (e.g., methylene blue) such as between 3-8 redox molecules, and (2) a spacer of between about 8 A and 20 A (and in particular between 10 A and 20 A), results in an assay that has one or more orders of magnitude greater signal and greater sensitivity as compared to prior DNA-based assays. The resulting sensitivity and signal are even greater when the concentration of the number of sensing molecules, which can be estimated based on the concentration of tether polynucleotide bound to the substrate, such as the concentration of thiol-DNA, is between 1 nM and 5 mM, an in particular is between 30 nM and 500 nM when multiple redox molecules are used in combination with spacers of between 8 and 20 A.

Prior work on DNA-based assays taught that the spacing between the signal moiety and the substrate should ideally be about 4 A, and certainly less than 8 A. For example, with a single redox molecule forming the signal moiety, spacing of 4 A, 6 A, 8 A and 10 A were examined and it was found that the 4 A spacing was significantly better than larger spacings, including in particular 6 A, 8 A and 10 A. 8 A and 10 A spacings did not result in significant suppression of signal (indicating binding of target "anchor" molecule to the target anchor recognition molecule). Surprisingly, as described herein, the use of multiple (e.g., between 2-10, between 3-8, between 5-10, about 5, etc.) signal moieties may increase signal, and in particular, may increase signal suppression (indicating binding of the target anchor molecule to the anchor recognition moiety) when spaced further from substrate, such as greater than 6 A, 8 A or 10 A (e.g., between 8 A and 20 A, between 10 A or 20 A, etc.). Previously such spacing was believed to result in a increasingly lower signal suppression.

Thus, in any of these apparatuses and methods, the signal moiety may comprise between 2 and 15 redox molecules. The signal moiety may comprise between 4-10 redox molecules. Each of the plurality of redox molecule may comprise a methylene blue molecule. The concentration of the thiol-DNA spacer may be between 1 nM and 5 uM. The single stranded tether region extends between 6 A and 20 A. For example, the signal moiety may comprise between 3 and 8 methylene blue molecules and wherein the single stranded tether region extends between 8 A and 20 A.

Also described herein are systems comprising: a continuous DNA molecule comprising a first hairpin structural motif attached to a second hairpin structural motif via a first segment of single stranded DNA; an anchor recognition moiety coupled to the continuous DNA molecule; a signal moiety comprising between 3 and 10 redox molecules, wherein the signal moiety is coupled to the continuous DNA molecule, wherein the signal moiety and the anchor recognition moiety are in effective proximity to each other; and a thiol-DNA spacer segment attached at a first end to the second hairpin structural motif such that it forms a single stranded tether region at one end of the single continuous DNA molecule extending between 8 A and 20 A; and an electrode having a surface, wherein the thiol-DNA spacer of the nanostructure is coupled at a second end to the to the surface in a concentration of between 1 nM and 5 uM.

As mentioned, the signal moiety may comprise between 4 and 8 redox molecules. Each of the plurality of redox molecules may comprises a methylene blue molecule. The concentration of the thiol-DNA spacer may be between 30 nM and 1 uM. The single stranded tether region may extend between 8 A and 20 A. The signal moiety may comprise between 3 and 8 methylene blue molecules and wherein the single stranded tether region extends between 10 A and 20 A.

Any of these methods may include the electrode(s) (e.g., the substrate) as part of an assay cartridge, insert, etc. that may be removably and/or replaceably included in a sensor that is configured to receive the substrate and connect it to a detector circuitry. The detector circuitry may include sensing electronics that detects the binding of a target molecule to the DNA-based nanostructure by detecting proximity of the redox molecule to the substrate (e.g., electrode) over time. The detector circuitry may therefore include amplification, signal processing (e.g., filtering, smoothing, etc.) and storage (e.g., memory) and may include one or more processors to review the electrical activity from the DNA-based nanostructure(s) bound to the substrate (e.g., electrodes).

Also described herein are methods of using any of these system and apparatuses. For example, a DNA nanostructure-based method may include: exposing a DNA-based nanostructure to a sample material comprising a target molecule, wherein the DNA-based nanostructure comprises: a continuous DNA molecule comprising a first hairpin structural motif attached to a second hairpin structural motif via a first segment of single stranded DNA; an anchor recognition moiety coupled to the continuous DNA molecule, wherein the anchor recognition moiety binds to the target molecule; a signal moiety comprising a plurality of redox molecules, wherein the signal moiety is coupled to the continuous DNA molecule, wherein the signal moiety and the anchor recognition moiety are in effective proximity to each other; and a thiol-DNA spacer segment attached at a first end to an electrically conductive substrate and at a second end to the second hairpin structural motif such that it forms a single stranded tether region at one end of the single continuous DNA molecule extending between 8 A and 20 A (e.g., 10 A and 20 A; and quantifying an amount of the target molecule by analyzing the electrochemical signal from the DNA-based nanostructure, wherein the electrochemical signal changes in proportion to changes in concentration of the target. The signal moiety may comprise between 2 and 15 redox molecules. The signal moiety may comprise between 4-10 redox molecules. Each of the plurality of redox molecule may comprise a methylene blue molecule. The concentration of the thiol-DNA spacer may be between about 1 nM and about 5 uM. The single stranded tether region may extend between 10 A and 20 A. The signal moiety may comprise between 3 and 8 methylene blue molecules and the single stranded tether region may extend between 3 A and 8 A.

As used herein the use of "#A" (as in 4 A, 6 A, 8 A, 10 A, etc.) refers to the distance of the plurality of redox molecules (tag) from the conductive surface, in nucleotides (specifically adenine) based on the sequence of the tether region of the DNA strand forming the DNA nanostructure-based assay. Thus the length of the tether region may be expressed as a number of nucleotides (adenine) in reference to the average distance of the redox molecules tag from the surface of the electrode. As mentioned, the distance may be between 8 A and 20 A, or between 10 A and 20 A, between 11 A and 20 A, between 12 A and 20 A, etc.

For example, described herein are methods and apparatuses (e.g., assays, systems, etc.) that provide highly sensitive DNA nanostructure-based assays. These methods may include: using a signaling DNA onto which multiple redox molecules have been attached; the spacer DNA may be optimized (e.g., within a predetermined size range) in order to modulate and/or enhance the signal change due to probe binding by controlling the distance of the redox molecules from the substrate before and after binding. The thiol DNA concentration may be optimized in order to shift the target measuring range appropriately for a given analyte.

In any of these methods, the method may include amending multiple redox molecules on a single signaling DNA for higher current signal.

Thus, in general, the signaling DNA may include a plurality of redox molecules; for example, the signaling DNA may comprise between 1 and 15 redox molecules. Any appropriate redox molecule may be used, such as (but not limited to) a methylene blue (MB) molecule.

The thiol DNA concentration may be between 1 nM and 5 uM.

In any of these methods and apparatuses (e.g., assays, systems, etc.), The spacer DNA may be between 8 A and 20 A (between 10 A and 20 A, between 11 A and 20 A, between 12 A and 20 A, etc.).

The methods and apparatuses described herein may be particularly sensitive. For example, these assays may be detect a target in the range of 1 pM-100 uM, which may not otherwise be detectable by a DNA-based assay without these modifications.

For example, described herein are methods including DNA nanostructure-based assay method, that include: performing a DNA-nanostructure based assay wherein each signaling DNA includes a plurality of redox molecules coupled thereto and configured for higher current signal, wherein the position of each redox molecule on the signaling DNA is adjusted based on spacer DNA for modulating the signal change during probe binding, further wherein the thiol DNA concentration of the signaling DNA is adjusted to shift the target measuring range based on the analyte. As mentioned, the signaling DNA may comprise between 1 and 15 redox molecules. The plurality of redox molecules may comprise methylene blue (MB). The thiol DNA concentration may be between 1 nM and 5 uM. In any of these methods and apparatuses, the spacer DNA may be between 8 A and 20 A. The target being measured may be in the range of 1 pM-100 uM.

All of the methods and apparatuses described herein, in any combination, are herein contemplated and can be used to achieve the benefits as described herein.

BRIEF DESCRIPTION OF THE DRAWINGS

A better understanding of the features and advantages of the methods and apparatuses described herein will be obtained by reference to the following detailed description that sets forth illustrative embodiments, and the accompanying drawings of which.

DETAILED DESCRIPTION

DNA-nanostructures can be used in an assay to detect and/or quantify an analyte of interest. A DNA-nanostructure can include a single DNA molecule composed of hairpin structural motifs, an anchor recognition moiety, and a signal moiety, where the anchor recognition moiety and the signal moiety are in effective proximity to each other such that the tethered diffusion of the signal molecule can be altered based upon binding status of the anchor recognition moiety.

A DNA-based electrochemical sensor can include a DNA-nanostructure that can include a single DNA molecule that includes at least two hairpin structural motifs whose stems are coupled together via a region of unhybridized DNA, an anchor recognition moiety that is coupled to the unhybridized region of DNA that couples the at last two hairpin structural motifs together, a signal moiety that is coupled to a 3' terminal end of one of the hairpin motifs, and a tether region that is configured to be attached to an electrode. When the anchor recognition moiety is unbound, the DNA-nanostructure moves in 3D space at a first frequency and/or speed defined by its tethered diffusion rate. Analyte binding is measured by detecting and/or measuring a change in the tethered diffusion rate as measured by analyzing the signal moiety. Thus, when the anchor recognition moiety is bound, directly or indirectly, by an analyte, the DNA-nanostructure moves in 3D space at a second frequency and/or speed, defined by its new tethered diffusion rate. The first and second frequencies and/or speeds are different from each other. The frequency/speed can be detected by measuring properties of the signal moiety, directly or indirectly.

Figure 1:
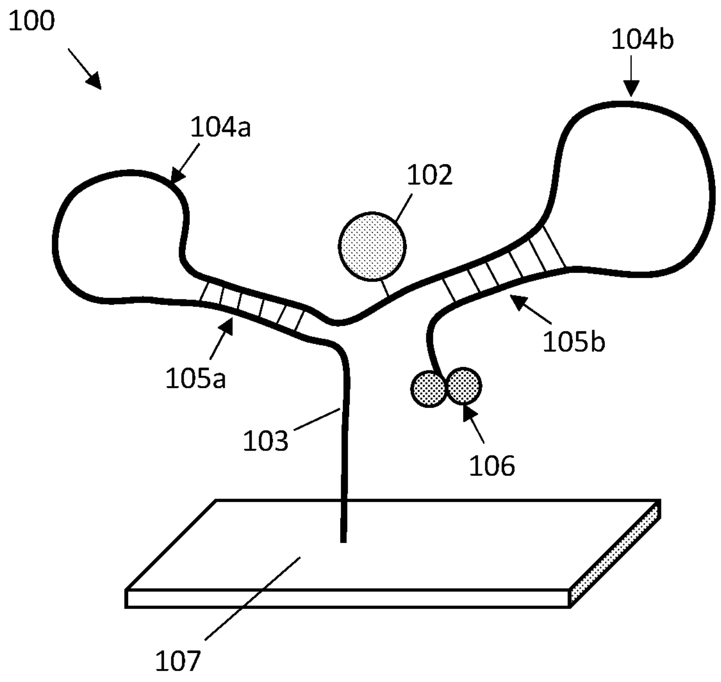
FIG. 1 schematically illustrates one example of a DNA-nanostructure as described herein.

DNA-nano structure can be generated from ligating two or more DNA molecules together to form the single molecule DNA-nanostructure. A DNA-nanostructure can detect a range of molecular classes of analytes. A DNA-nanostructure can be used in assays to detect and/or measure an analyte of interest. FIG. 1 shows one example of DNA-nanostructure 100 including a single continuous DNA molecule that can have specialized structural regions (e.g. hairpin motifs 101_a,b_, stems 105_a,b_, anchor recognition moiety 102, a signal moiety 106, and a tether 103). The anchor recognition moiety 102 and signal moiety 106 can be attached to the DNA-nanostructure in positions that place the anchor recognition moiety and the signal moiety in effective proximity to each other such that a change in the binding status of the anchor recognition moiety results in a change in the tethered diffusion of the signal moiety relative to the substrate 107, which can be measured and provide feedback on the binding status of the anchor recognition moiety. In this way binding of an analyte of interest to the DNA-nanostructure can be detected and measured. Each of the signal moiety and anchor recognition moiety can be coupled to the polynucleotide that can make up the DNA-nanostructure at any position so long as their positions relative to one another put them in effective proximity to each other as described elsewhere herein.

The recognition moiety may be, for example, one or more of an aptamer, an antibody, an antibody/DNA conjugate, and/or a combination thereof. In general, the recognition moiety may be specific to the target to be identified. Although virtually any target molecule may be used, including protein or peptide targets, specific and non-limiting examples of targets may include serum amyloid A-1 (SAA-1), MR-proADM, and NT-proBNP.

The DNA-nanostructure can include at least two hairpin structural motifs 101_a,b_ (collectively 101). The hairpin structural motifs 101 each can be composed of a stem 105 a, b (collectively 105) and a loop 104 a, b (collectively 104) region. The loop in each hairpin motif contains unpaired nucleotides. The loop in each hairpin motif can contain 1 to 100 nucleotides, with a preferred range of 4 to 20 nucleotides to promote efficient intramolecular hybridization, i.e. hairpin formation, during nanostructure construction or synthesis. The loop in each hairpin motif can be composed of a wide range of nucleotide sequences. In aspects, the nucleotide sequence can limit or completely eliminate formation of a secondary structure within the loop and also can limit or completely eliminate interactions with any other portion of the nanostructure. A non-limiting example of such a nucleotide sequence can be is a poly-adenosine-monophosphate (polyA) sequence. In some aspects, additional nucleic acid elements can be attached or otherwise incorporated into the loop or other portion of the hairpin motif. In a non-limiting example, the sequence of the loop a can be 5' . . . . CAA GAA CT . . . 3', and one example of the loop b is 5' . . . . ACT GTG TC . . . 3'. In some aspects, the loop in each hairpin motif can be comprised of a different polymer or biopolymer. One example would be to use a polyethylene glycol (PEG) chain instead of a nucleic acid loop in this region of the nanostructure.

The stem of each hairpin motif is composed of complementary DNA regions that are 90-100% complementary of each other and hybridized through conventional base-pair bonding. The stem of each hairpin motif can contain 2 to 100 nucleotides on each complementary DNA region, with a preferred range of 10 to 30 nucleotides to minimize the nanostructure's size while also promoting its assembly and ligation-based synthesis at the surface. In aspects the preferred Tm (melting temperature) of a stem and/or hairpin motif can be between 15 to 60 degrees Celsius (C) prior to ligation and/or hybridization. After ligation and/or hybridization, the complex becomes more stable with a Tm typically greater than 70 degrees C. In some aspects, the Tm of a of a stem 105a and/or 105b and/or hairpin motif can be about 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 31.5, 32, 32.5, 33, 33.5, 34, 34.5, 35, 35.5, 36, 36.5, 37, 37.5, 38, 38.5, 39, 39.5, 40, 40.5, 41, 41.5, 42, 42.5, 43, 43.5, 44, 44.5, 45, 45.5, 46, 46.5, 47, 47.5, 48, 48.5, 49, 49.5, 50, 50.5, 51, 51.5, 52, 52.5, 53, 53.5, 54, 54.5, 55, 55.5, 56, 56.5, 57, 57.5, 58, 58.5, 59, 59.5, to/or about 60 degrees C. prior to ligation. In some aspects, the complex becomes more stable after ligation and/or hybridization and can have a Tm of about 70, 70.5, 71, 71.5, 72, 72.5, 73, 73.5, 74, 74.5, 75, 75.5, 76, 76.5, 77, 77.5, 78, 78.5, 79, 79.5, 80, 80.5, 81, 81.5, 82, 82.5, 83, 83.5, 84, 84.5, 85, 85.5, 86, 86.5, 87, 87.5, 88, 88.5, 89, 89.5, or/to about 90 degrees C.

The stem can be composed of a nucleotide sequence. In aspects, the stem nucleotide sequence can promote complementary hybridization (e.g. double-stranded DNA) in the stem region while also limiting or completely eliminating interactions with any other portion of the nanostructure. By way of a non-limiting example, in aspects the sequence of the stem 105a can be 5'- . . . CACAGCCT-CACCTCTTCCTA . . . -3' (SEQ ID NO: 12) and its complementary sequence; and the stem 105b can be 5'- . . . GTCTCCGGTTGAAGTGGAGA . . . -3' (SEQ ID NO: 13) and its complementary sequence.

The DNA composing the hairpin motifs can include unmodified or modified nucleotides. Suitable base modifications include, but are not limited to 2-aminopurine, 2,6-diaminopurine, 5-bromo-deoxyuridine, deoxyuridine, inverted dT, inverted Dideoxy-T, Dideoxycytidine, 5-methyl deoxycytidine, deoxyinosine, 5-hydroxybutynl-2'-deoxyuridine, 8-aza-7-deazaguanosine, 5-nitroindole, hydroxymethyl dC, Iso-dC, Iso-dG, 2' fluoro bases, 2'-O-methoxy-ethyl Bases (2'MOEs). The specific DNA sequence of each hairpin motif can be readily generated by one of ordinary skill in the art based at least upon the parameters and functional aspects of at least the hairpin structural motifs and/or DNA-nanostructure discussed here and elsewhere herein. Commercially available DNA motif and hairpin design tools can be used to generate specific sequences that would form hairpin structures with the appropriate number of paired and unpaired nucleotides according to this disclosure. Such commercially available design tools can include EGNAS (Kick et al., BMC Bioinformatics. 2012. 13:138) or NUPACK (J. N. Zadeh, et al., J Comput Chem, 32:170-173, 2011). In some aspects, the hairpin motifs have the same DNA sequence. In some aspects the hairpin motifs have a different DNA sequence than each other. In some aspects, the DNA sequence between any two hairpin motifs are completely different from one another. In some aspects, the hairpin motifs differ from each other in 1, 2, 3, 4, 5, 6, 7, 8, 9, 10, 11, 12, 13, 14, 15, 16, 17, 18, 19, 20, 21, 22, 23, 24, 25, or more nucleotides.

The two (or more) hairpin motifs can be coupled to each other directly (without unpaired nucleotides) or by an unhybridized (or unpaired) region of DNA (e.g. a region of single stranded DNA) between the stem region of one hairpin motif and the stem region of a second hairpin motif. This coupling region can include 0 to 100 nucleotides, or more nucleotides. A preferred coupling region would include 0 to 10 nucleotides to minimize the nanostructure size and maintain structural consistency. In aspects, the unhybridized region can be formed from a 3' tail of one hairpin motif and a 5' tail of a second hairpin motif that are ligated together during formation of the DNA-nanostructure. It will be appreciated that where the structure is described with respect to the 5' and 3' ends or direction, that the is also the same. In short, as long as the secondary structure can be attained, the read direction of the underlying nucleotide sequences can be either direction.

For example, in FIG. 1 the ends of the DNA nanostructure can be either 5' or 3' based on the chemical structure of the polynucleotide. The 3' (or 5', when the reverse polynucleotide is considered) end of a stem of one of the DNA structural motifs can be coupled to a tether. The tether can be a DNA strand that can be configured to optionally couple to a substrate 107, which may be an electrode surface. The length of the tether can, in aspects where the tether is coupled to an electrode surface, keep the anchor recognition portion at a distance from the substrate (e.g., electrode surface) such that the signal moiety 106 is at a suitable distance from the electrode surface. The tether can include a linkage from the surface to the double-stranded stem region 105a, such as a polymer chain or carbon chain. The tether can also include unhybridized single stranded DNA. If so, the tether can include 0, 1, 2, 3, 4, 5, 6, 7, 8, 9, 10, 11, 12, 13, 14, 15, 16, 17, 18, 19, or 20 nucleotides. Each of the nucleotides in the tether can be unmodified or modified bases. Suitable base modifications include, but are not limited to 2-aminopurine, 2,6-diaminopurine, 5-bromo-deoxyuridine, deoxyuridine, inverted dT, inverted Dideoxy-T, Dideoxycytidine, 5-methyl deoxycytidine, deoxyinosine, 5-hydroxybutynl-2'-deoxyuridine, 8-aza-7-deazaguanosine, 5-nitroindole, hydroxymethyl dC, Iso-dC, Iso-dG, 2' fluoro bases, 2'-O-methoxy-ethyl Bases (2'MOEs).

The 3' (or 5', when considering the reverse polynucleotide) end of the tether can be optionally modified or coupled to a linking moiety that renders the tether capable of coupling to a support or electrode surface. Suitable linking moieties linking moieties can include, or include after a suitable reaction, a suitable reactive group. Many suitable reactive groups are generally known to those of ordinary skill in the art. Suitable reactive groups include, but are not limited to, a carboxyl group, amino group, aromatic amine group, a chloromethyl group, an amide group, a hydrazide group, a hydroxyl, a thiol, an epoxy or a combination thereof. In particular, the linking moiety may be thiol. Thus the tether may be a thiol-DNA. These groups can be incorporated to the tether using a reaction that will be instantly appreciated by one of ordinary skill in the art. The tether can be attached to a support or electrode surface using a suitable reaction that will be instantly appreciated by one of ordinary skill in the art based, at least in part, on the reactive group used and the chemical nature of the support or electrode surface.

The nucleic acid nanostructure can have any polynucleotide sequence that results in the formation of the general secondary structures as depicted in FIG. 1. For example, a tether can be unattached or can be attached to a conductive substrate surface, such as an electrode. The tether may be linked to a stem with a loop. A second stem and loop are used to provide structural consistency and to aid in nanostructure assembly and synthesis. The anchor recognition moiety should be positioned near the signal moiety. The positioning of these moieties relative to the nanostructure is not necessarily fixed, although a convenient positioning is to place them in between the two stems.

SEQ IDs NO. 1-4 provide non-limiting examples of tether portions of the DNA-based nanostructures described herein, having 4 A, 6 A, 8 A and 10 A spacings, respectively. SEQ ID NO. 5 is an example of a sequence of an anchor region (in this example, a Tacrolimus binding anchor region). SEQ ID NO. 6 is an example of a sequence of a signal moiety portion of a DNA sensor, having a single signal moiety, in this case MB. SEQ ID NO. 7 is another example of a sequence of a signal moiety portion of a DNA-based nanostructure, having five MB signal moieties. SEQ IDs NO. 8-11 illustrate just the DNA sequences of the fully conjugated DNA-based nanostructures for 4 A, 6 A, 8 A, and 10 A examples, respectively.

The DNA-nanostructure can have a polynucleotide sequence prior to optional base modification that is about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% to 100% identical to any one of SEQ ID NOs: 1-11. It will be appreciated that any primary polynucleotide sequence is acceptable such that it can generate the secondary structure as described elsewhere herein. In some aspects, the DNA-nanostructure can have a polynucleotide sequence prior to any optional base modification that does not share any identity with SEQ ID NOs: 1-11, as long as the primary polynucleotide sequence is acceptable such that it can generate the secondary structure as described elsewhere herein. Suitable primary polynucleotide sequences corresponding to the secondary structures described and demonstrated herein can be designed and analyzed using the NUPACK software suite, which can allow the analysis and rational design of nucleic acid structures based on the equilibrium base-pairing properties of interacting nucleic acid strands. The NUPACK software suite is available at nupack.org and is further discussed in Zadeh et al., NUPACK: analysis and design of nucleic acid systems. J Comput Chem, 32:170-173, 2011, Dirks et al., Thermodynamic analysis of interacting nucleic acid strands. SIAM Rev, 49:65-88, 2007; Dirks and Pierce, An algorithm for computing nucleic acid base-pairing probabilities including pseudoknots. J Comput Chem, 25:1295-1304, 2004; Dirks and Pierce, A partition function algorithm for nucleic acid secondary structure including pseudoknots. J Comput Chem, 24:1664-1677, 2003; Wolfe et al., Constrained multistate sequence design for nucleic acid reaction pathway engineering. J Am Chem Soc, 139:3134-3144, 2017; Wolf and Pierce, Sequence design for a test tube of interacting nucleic acid strands. ACS Synth Biol, 4:1086-1100, 2015; Zadeh et al., Nucleic acid sequence design via efficient ensemble defect optimization. J Comput Chem, 32:439-452, 2011; and Dirks et al., Paradigms for computational nucleic acid design. Nucl Acids Res, 32:1392-1403, 2004.

The DNA-nanostructure can be configured to bind directly to analyte of interest or indirectly (i.e. through an anchor molecule that can directly bind the analyte of interest). To accomplish this, the anchor recognition moiety can be configured to specifically bind the analyte of interest or bind an anchor molecule. Analytes of interest can include small molecule chemical (organic or inorganic) compounds, drugs, DNA molecules, RNA molecules, peptides, and proteins. The analyte of interest can be determined by a user of the DNA nanostructure and can serve as the basis for directing a user or one of ordinary skill in the art to determine the appropriate components of the DNA-nanostructure and system thereof described herein in view of this disclosure using techniques generally known in the art. Similarly, anchor recognition moiety molecules of interest can include small molecule chemical (organic or inorganic) compounds, drugs, DNA molecules, RNA molecules, peptides, and proteins. The anchor recognition moiety of interest can be determined by a user of the DNA nanostructure and can serve as the basis for directing a user or one of ordinary skill in the art to determine the appropriate components of the DNA-nanostructure and system thereof described herein in view of this disclosure using techniques generally known in the art.

Exemplary analytes of interest will therefore be the same or similar to exemplary anchor recognition moieties; these include, but are not limited to, small molecule drugs such as tamoxifen, atorvastatin, apremilast, morphine, etc.; peptide drugs such as exendin-4, NA-1, insulin analogs, etc.; larger protein or antibody therapeutics such as insulin, pembrolizumab, rituximab, etc.; biomarkers such as cortisol, neuropeptide-Y, IFN-gamma, C-peptide, glucagon, somatostatin, C-reactive protein, natriuretic peptides, creatine kinase, procalcitonin, etc.; immune markers such as tissue transglutaminase antibodies, anti-nuclear antibodies, etc.; toxins such as ricin, alpha-amanitin, etc.; biotechnology reagents such as biotin, streptavidin, digoxigenin, etc. Due to the generalizability of the nanostructure, there is a very wide range of analytes and anchor recognition moieties that are potentially of interest.

Anchor molecules are molecules that can either be the analyte of interest (as part of the sample), or be a binding partner of the analyte of interest, or be an analog that is similar to the analyte of interest. Anchor molecules should specifically bind to the anchor recognition moiety on the DNA-nanostructure. In a similar way, the anchor recognition moiety can either have the same or similar structure as the analyte of interest, or be a binding partner of the analyte of interest, or be an analog that is similar to the analyte of interest. The use of an anchor molecule can allow for, among other things that will be appreciated by one of ordinary skill in the art in view of this disclosure, configuration of the assay as a "signal OFF" (i.e., where the assay begins with the anchor molecule not bound to the anchor recognition moiety and binding turns the signal "off") or as a "signal ON" (i.e. where the assay begins with the anchor molecule bound to the anchor recognition moiety and binding of an analyte of interest results in the anchor molecule disassociating with the anchor recognition moiety and turns the signal "on") assay. Suitable anchor molecules include antibodies, aptamers, affibodies, proteins, peptides, nucleic acids, polymers, particles, beads, cells, and fragments thereof, that can specifically bind an analyte of interest and the anchor recognition moiety.

Exemplary anchor molecules include, but are not limited to, streptavidin, anti-digoxigenin, anti-insulin, anti-exendin-4, anti-C-peptide, tissue transglutaminase antibodies, anti-nuclear antibodies, insulin, pembrolizumab, rituximab, IFN-gamma, ricin, anti-thrombin aptamers, anti-ATP aptamers, anti-cocaine aptamers, miRNA-375, mannose-binding lectins, gold nanoparticles, cancer cells, bacterial pathogens, viral particles, etc. Due to the generalizability of the nanostructure, there is a very wide range of anchor molecules that are potentially of interest. The DNA-nanostructure can include a signal moiety, and specifically a redox molecule, such as (but not limited to) methylene blue (MB). The signal moiety can cause a signal to be produced, e.g. via a redox reaction or resonance-based reaction (e.g. FRET) at an electrode surface or support surface. The tethered diffusion can be measured via measuring the signal produced from the signal moiety directly.

A signal produced from the signaling moiety can be directly measured if the signal moiety is attached to a support or an electrode surface. Changes in the frequency or position of interaction of the signaling moiety with the support or electrode surface (e.g. due to the anchor recognition moiety being bound or not) can result in a change in the output signal from the signaling moiety and can be used to detect and/or quantify presence of an analyte.

The tethered diffusion can also be quantified by measuring an output from an electrode, where the electrode is stimulated to produce and/or modulate an output when a signal moiety interacts with an electrode surface. The interaction at the electrode surface can be a chemical (e.g. a redox) reaction that can occur when the signaling moiety is in proximity to the electrode surface such that a reaction can occur. Changes in the frequency or position of interaction of the signaling moiety with the electrode surface (e.g. due to the anchor recognition moiety being bound or not) can result in a change in the output signal from the electrode, which can be used to detect and/or quantify presence of an analyte.

Suitable redox molecules include, but are not limited to methylene blue, nile blue, anthraquinone, ferrocene, ferricyanide/ferrocyanide, etc.

The DNA-nanostructure can be attached to a support structure or an electrode surface. The support structure or electrode can be any suitable shape or design. In aspects, the electrode is a support structure. The DNA-nanostructure can be attached to the support structure or an electrode surface via the tether. As previously discussed, the tether can have a 3' linker or modified nucleotide(s) that can provide a reactive group that can be used to attach the tether to the support structure or an electrode surface.

Suitable support structures can be any solid or semi-solid (e.g. hydrogel) material. Suitable materials include glass, ceramics, metals, metal oxides, metal alloys, polymeric materials (polymers, copolymers, composite polymers, polymer blends, etc.), mixtures thereof and composites thereof. Metals can include, but are not limited to, the alkali metals, alkaline earth metals, transition metals, rare earth metals, combinations thereof, mixtures thereof, and composites thereof. In aspects, the metal or metal composite, oxide, alloy, or mixture thereof can be or include gold, aluminum, copper, iron, lead, silver, platinum, zinc, and/or nickel. Suitable polymeric materials can include, but are not limited to, natural and synthetic polymeric materials. Natural polymeric materials can include, but are not limited to, polysaccharides, natural rubber, polylacticacid, polylysine, polyglutamate, polyornithine, polyarginine, polyaspartate, polyhistidine, polylactide, etc. Synthetic polymers include, but are not limited to, polyethylene, polypropolyene, polystyrene, polyvinyl chloride, synthetic rubber, phenol formaldehyde resin, silicone, polyacrylonitrile, polystyrene, polytetrafluoroethylene, polyurethanes, polyethylene terephthalate, and combinations, copolymers, and blends thereof. The polymeric material can be a thermoplastic, thermoset, elastomer, or a permissible combination thereof.

The electrode and/or electrode surface can be made of any suitable material. In aspects, the suitable material is electrically conductive. In some aspects, electrode and/or electrode surface can be made of a metal, metal oxide, metal composite, metal alloy, or a combination thereof. Metals can include, but are not limited to, the alkali metals, alkaline earth metals, transition metals, rare earth metals, combinations thereof, mixtures thereof, and composites thereof. In aspects, the metal or metal composite, oxide, alloy, or mixture thereof can be or include gold, aluminum, copper, iron, lead, silver, platinum, zinc, and/or nickel.

Generation of the DNA-based nanostructure can begin by separately generating three separate components that can be brought together to form the single molecule DNA-nanostructure. A first partial hairpin DNA with about 1-50, with a preferred range of 3-15, bases hybridized in the stem region can be generated by any suitable DNA synthesis technology (e.g. any recombinant or de novo synthesis technique). The 3' (or 5' end when considering the reverse) end can be optionally modified with a suitable linker or contain one or more modified nucleotides, where the linker or modification provides a reactive group to allow for optional attachment to a support structure or electrode surface. Suitable linkers/modifications are described elsewhere herein. Where the DNA-nanostructure is optionally coupled to a support or electrode surface, the first partial hairpin DNA can be coupled to the support or electrode surface prior to further assembly of the DNA-nanostructure. Any primary polynucleotide sequence is acceptable such that it can be assembled with other DNA-nanostructure components described elsewhere herein and generate the secondary structure as described elsewhere herein. The first partial hairpin can have a polynucleotide sequence, as long as the primary polynucleotide sequence is acceptable such that it can be assembled with other DNA-nanostructure components described elsewhere herein and generate the secondary structure as described elsewhere herein.

A second partial hairpin DNA with about 1-50, with a preferred range of 3-15, bases can be hybridized in the stem region can be generated by any suitable DNA synthesis technology (e.g. any recombinant or de novo synthesis technique), which will be appreciated by one of ordinary skill in the art in view of this disclosure. This second partial hairpin DNA is also referred to herein as an anchor recognizing unit. The second partial hairpin DNA can have one or more modified bases that can incorporate a reactive group or a linker that can contain a reactive group that can be capable of coupling an anchor recognition moiety. The modified base may include an anchor recognition moiety coupled to the modified base. The modified base can be any non-5' (or 3' when considering the reverse) terminal base. The modified base can be any internal (i.e., not the terminal 5' or 3' base). Thus, the anchor recognition moiety may be incorporated in the DNA-nanostructure once assembled without needing further post-assembly reactions to attach the anchor recognition moiety. Suitable base modifications include, but are not limited to 2-aminopurine, 2,6-diaminopurine, 5-bromodeoxyuridine, deoxyuridine, inverted dT, inverted Dideoxy-T, Dideoxycytidine, 5-methyl deoxycytidine, deoxyinosine, 5-hydroxybutynl-2'-deoxyuridine, 8-aza-7-deazaguanosine, 5-nitroindole, hydroxymethyl dC, Iso-dC, Iso-dG, 2' fluoro bases, 2'-O-methoxy-ethyl Bases (2'MOEs). Many suitable reactive groups are generally known to those of ordinary skill in the art. Suitable reactive groups include, but are not limited to, a carboxyl group, amino group, aromatic amine group, a chloromethyl group, an amide group, a hydrazide group, a hydroxyl, a thiol, an epoxy, an azide, click chemistry modifications, or a combination thereof.

A single stranded DNA molecule can be generated that is configured to partially hybridize to the second partial hairpin DNA molecule. The single stranded DNA molecule can be generated by any suitable DNA synthesis technology (e.g. any recombinant or de novo synthesis technique), which will be appreciated by one of ordinary skill in the art in view of this disclosure. The single stranded DNA molecule can include a signal molecule. The signal molecule can be coupled to the 5' end of the single stranded DNA molecule. Suitable signal molecules are described elsewhere herein. The signal molecule can be coupled to the 5' end via coupling to a modified or unmodified 5' terminal base or linker attached to 5' terminal base. The modification can provide a reactive group that can be used to couple, directly or indirectly via a linker, a signal moiety to the 5' terminal base. In aspects, the linker can contain a reactive group that can couple to a signal moiety. Suitable base modifications include, but are not limited to 2-aminopurine, 2,6-diaminopurine, 5-bromo-deoxyuridine, deoxyuridine, inverted dT, inverted Dideoxy-T, Dideoxycytidine, 5-methyl deoxycytidine, deoxyinosine, 5-hydroxybutynl-2'-deoxyuridine, 8-aza-7-deazaguanosine, 5-nitroindole, hydroxymethyl dC, Iso-dC, Iso-dG, 2' fluoro bases, 2'-O-methoxy-ethyl Bases (2'MOEs). Many suitable reactive groups are generally known to those of ordinary skill in the art. Suitable reactive groups include, but are not limited to, a carboxyl group, amino group, aromatic amine group, a chloromethyl group, an amide group, a hydrazide group, a hydroxyl, a thiol, an epoxy, an azide, click chemistry modifications, or a combination thereof. The single stranded DNA molecule can be modified prior to DNA-nanostructure assembly to include a signal moiety. In other aspects, the signal moiety can be coupled to the DNA-nanostructure after assembly.

The assembly of the DNA-nanostructure from the three components (whether coupled to a support structure or electrode surface or not) can occur in some aspects via self-assembly driven by equilibrium. Although this can result in assembly of the DNA-nanostructure, this process is inefficient. A suitable DNA ligase can be used to assemble the components of the DNA-nanostructure in a non-equilibrium manner. Suitable DNA ligases include, but are not limited to, T4 DNA ligase, T7 DNA ligase, Taq DNA ligase, Electroligase, HiFi Taq DNA ligase, NxGen T4 DNA ligase, Ampligase, and T4 RNA ligase 2. In aspects, the three components of the DNA-nanostructure can be included in a reaction and contacted with an amount of a suitable DNA ligase and, under suitable reaction conditions, allowed to react with the DNA ligase to form the single molecule DNA-nanostructure. The volume and the concentration can be maneuvered, preferably 1 nM to 20 μM concentration of the components can be used, with the volume of 1 to 1000 μL. A ligase concentration of 1 to 100,000 U can be used. The preferred temperature of ligase reaction is 15 to 50 degrees C. The DNA-nanostructures described herein can be made by any other suitable technique that will be appreciated by one of ordinary skill in the art in view of the instant description of the DNA-nanostructures herein.

The DNA-nanostructures described herein can be used in an assay to detect and/or quantify an analyte of interest. Suitable analytes of interest are described elsewhere herein. In general, the DNA-nanostructure can be contacted, directly or indirectly (e.g. via an anchor molecule) with a sample containing or is suspected of containing an analyte of interest. The sample can be a fluid. Solid samples of interest can be put into a liquid mixture or solution for analysis. Samples can be obtained from any suitable source, including but not limited to, a subject or an inanimate object or source (e.g. object source, soil, water source, air etc.). In some aspects, the sample is a complex sample (e.g. containing many types of compounds, molecules, and the like), such as blood or a component thereof (e.g. serum or plasma), soil, unfiltered water from a water source, etc. The sample can be filtered by a suitable method prior to contact with the DNA-nanostructure. Suitable filtering methods include, but are not limited to, size separation-based methods (e.g. membrane-based, chromatography, and electrophoretic methods), charge separation-based methods e.g. membrane-based, chromatography, and electrophoretic methods), affinity purification methods (e.g. antibody, aptamer, magnetic, etc. based purification methods).

After contacting the DNA-nanostructure, directly or indirectly, with the sample that can contain or is suspected of containing an analyte of interest, the analyte of interest, if present, can bind the anchor molecule or anchor recognition moiety. If an anchor molecule is used, an anchor molecule containing a bound analyte can bind the anchor recognition moiety on the DNA-nano structure. Binding of an analyte of interest or an anchor molecule bound to an analyte of interest can result in a change in tethered diffusion of the DNA-nanostructure as previously described. The signal produced, either directly or indirectly, from the signal moiety can be measured and used to indicate presence (or absence) of an analyte of interest and/or quantify an amount of an analyte of interest in a sample.

The assay can operate based on direct binding of an analyte of interest to the anchor recognition moiety and/or indirect detection of the analyte of interest. The analyte of interest can specifically bind the anchor recognition moiety. In other aspects, the analyte of interest can specifically bind an anchor molecule. The binding of an analyte of interest to the anchor molecule can result in a conformational change in the anchor molecule, which allows it to then specifically bind to the anchor recognition moiety. Binding of an analyte of interest to the anchor molecule may not result in a conformational change in the anchor molecule. The assay can include any suitable number of rinses or washes to remove unbound analyte of interest between steps of sample incubation and signal measurement. The number of washes can range from 1 to 100. Suitable buffers can include, but are not limited to, phosphate buffered saline, HEPES, cell media, Tris, Tris-EDTA, or any buffer known by those skilled in the art that will not interfere with the measurement of interest.

The signal moiety may be a redox molecule that produces a chemical change (e.g. a redox reaction) with a suitable surface or other molecule which can be translated into a signal by an electrode and/or detector. The signal moiety may be an energy donor molecule that can react with an optically active energy acceptor that can be coupled to a support and/or photodetector and stimulate production of a detectable optical signal from the optically active energy acceptor via energy transfer from the signal moiety to the energy acceptor molecule when they are in effective proximity to each other. The signal produced from the energy acceptor molecule can be detected by, e.g., a photodetector. A change in the signal and/or frequency of signal production either produced via a chemical (e.g. redox) reaction or optically can be used to determine presence and/or quantify amount of an analyte of interest as previously discussed. A change in the electrochemical reaction rate can be used to determine the presence and/or quantify the amount of an analyte of interest. This can be measured by a change in the current, such as an SVW current, that can be applied to an electrode.

Properties of the redox molecules can be interrogated with any electrochemical quantification technique, including but not limited to cyclic voltammetry (CV), linear sweep voltammetry, pulse voltammetry, chronoamperometry, square wave voltammetry (SWV), differential pulse voltammetry (DPV), AC voltammetry, fast-scan CV, etc. For interrogating the DNA-nanostructure, one possible algorithm to follow is to first measure the initial signal without analyte present. The target introduction will then induce binding of the anchor molecule, thereby shifting the output from the initial level. The percentage of shift or the magnitude of the shift, compared to the initial signal, is proportional to the target concentration. The target introduction could also induce displacement of the anchor molecule, thereby shifting the output from the initial level, and the percentage of shift or the magnitude of the shift, compared to the initial signal, is proportional to the target concentration. Specific examples using SVVV are given below.

Components of the assay described herein can be provided as a combination kit. The combination kit can include a DNA-nanostructure as described herein and an optional anchor molecule. The kit can also include solutions, diluents, buffers, reagents, containers, membranes, plates (e.g. 6, 12, 24, 48, 64, 96, 384 well plates), that can be used in sample preparation and/or assay performance.

Various modifications and variations of the described compositions, methods, and assays, and kits of the invention will be apparent to those skilled in the art without departing from the scope and spirit of the disclose. Although the various aspects of the DNA-nanostructure, systems thereof, manufacture thereof, and uses thereof have been described it will be understood that they can be further modified and that the invention as claimed should not be unduly limited to such specific aspects. Indeed, various modifications of the described modes for carrying out the invention that are obvious to those skilled in the art are intended to be within the scope of the invention. This application is intended to cover any variations, uses, or adaptations of the invention following, in general, the principles of the disclosure and including such departures from the present disclosure come within known customary practice within the art to which the disclosure pertains and can be applied to the essential features herein before set forth.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As used herein, "antibody" can refer to a glycoprotein containing at least two heavy (H) chains and two light (L) chains inter-connected by disulfide bonds, or an antigen binding portion thereof. Each heavy chain is comprised of a heavy chain variable region (abbreviated herein as VH) and a heavy chain constant region. Each light chain is comprised of a light chain variable region and a light chain constant region. The VH and VL regions retain the binding specificity to the antigen and can be further subdivided into regions of hypervariability, termed complementarity determining regions (CDR). The CDRs are interspersed with regions that are more conserved, termed framework regions (FR). Each VH and VL is composed of three CDRs and four framework regions, arranged from amino-terminus to carboxy-terminus in the following order: FR1, CDR1, FR2, CDR2, FR3, CDR3, and FR4. The variable regions of the heavy and light chains contain a binding domain that interacts with an antigen. "Antibody" includes single valent, bivalent and multivalent antibodies. "Antibody" also includes antibody fragments, such as Fab fragments. The term "Fab", as used herein, refers to antibody fragments including fragments which comprise two N-terminal portions of the heavy chain polypeptide joined by at least one disulfide bridge in the hinge region and two complete light chain polypeptides, where each light chain is complexed with one N-terminal portion of a heavy chain. Fab also includes Fab fragments which comprise all or a large portion of a light chain polypeptide (e.g., $V_LC_L$) complexed with the N-terminal portion of a heavy chain polypeptide (e.g., $V_HC_{H1}$).

As used herein, "aptamer" can refer to single-stranded DNA or RNA molecules that can bind to pre-selected targets including proteins with high affinity and specificity. Their specificity and characteristics are not only determined by their primary sequence, but also by their tertiary structure.

As used herein, "attached" can refer to covalent or non-covalent interaction between two or more molecules. Non-covalent interactions can include ionic bonds, electrostatic interactions, van der Walls forces, dipole-dipole interactions, dipole-induced-dipole interactions, London dispersion forces, hydrogen bonding, halogen bonding, electromagnetic interactions, 7-7 interactions, cation-7 interactions, anion-7 interactions, polar 7-interactions, and hydrophobic effects.

The term "carboxyl" is as defined above for the formula:

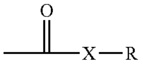

or

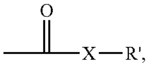

and is defined more specifically by the formula —RivCOOH, wherein Riv is an alkyl, alkenyl, alkynyl, cycloalkyl, heterocyclyl, alkylaryl, arylalkyl, aryl, or heteroaryl. In preferred embodiments, a straight chain or branched chain alkyl, alkenyl, and alkynyl have 30 or fewer carbon atoms in its backbone (e.g., C1-030 for straight chain alkyl, C3-C30 for branched chain alkyl, C2-C30 for straight chain alkenyl and alkynyl, C3-C30 for branched chain alkenyl and alkynyl), preferably 20 or fewer, more preferably 15 or fewer, most preferably 10 or fewer. Likewise, preferred cycloalkyls, heterocyclyls, aryls and heteroaryls have from 3-10 carbon atoms in their ring structure, and more preferably have 5, 6 or 7 carbons in the ring structure. The term "substituted carboxyl" refers to a carboxyl, as defined above, wherein one or more hydrogen atoms in R are substituted. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

As used herein, "deoxyribonucleic acid (DNA)" and "ribonucleic acid (RNA)" can generally refer to any polyribonucleotide or polydeoxribonucleotide, which may be unmodified RNA or DNA or modified RNA or DNA. RNA can be in the form of non-coding RNA such as tRNA (transfer RNA), snRNA (small nuclear RNA), rRNA (ribosomal RNA), anti-sense RNA, RNAi (RNA interference construct), siRNA (short interfering RNA), microRNA (miRNA), or ribozymes, aptamers, guide RNA (gRNA) or coding mRNA (messenger RNA).

As used herein, "derivative" can refer to any compound having the same or a similar core structure to the compound but having at least one structural difference, including substituting, deleting, and/or adding one or more atoms or functional groups. The term "derivative" does not mean that the derivative is synthesized from the parent compound either as a starting material or intermediate, although this may be the case. The term "derivative" can include prodrugs, or metabolites of the parent compound. Derivatives include compounds in which free amino groups in the parent compound have been derivatized to form amine hydrochlorides, p-toluene sulfoamides, benzoxycarboamides, t-butyloxycarboam ides, thiourethane-type derivatives, trifluoroacetylam ides, chloroacetylam ides, or formam ides. Derivatives include compounds in which carboxyl groups in the parent compound have been derivatized to form methyl and ethyl esters, or other types of esters or hydrazides. Derivatives include compounds in which hydroxyl groups in the parent compound have been derivatized to form O-acyl or O-alkyl derivatives. Derivatives include compounds in which a hydrogen bond donating group in the parent compound is replaced with another hydrogen bond donating group such as OH, NH, or SH. Derivatives include replacing a hydrogen bond acceptor group in the parent compound with another hydrogen bond acceptor group such as esters, ethers, ketones, carbonates, tertiary amines, imine, thiones, sulfones, tertiary amides, and sulfides. "Derivatives" also includes extensions of the replacement of the cyclopentane ring with saturated or unsaturated cyclohexane or other more complex, e.g., nitrogen-containing rings, and extensions of these rings with side various groups.

As used herein, "DNA molecule" includes nucleic acids/polynucleotides that are made of DNA.

As used herein, "effective proximity" refers to the distance or range of distances that can exists between two or more molecules where an interaction or reaction between the two molecules occurs that generates a measurable response. In the context of this disclosure, the effective proximity of a signal moiety and an anchor recognition moiety is the distance or range of distances between the two moieties where binding of the anchor recognition moiety by an analyte of interest or an anchor molecule can modulate the tethered diffusion of the signal moiety such that a measurable change in a signal produced, directly or indirectly, by the signal moiety can be detected and/or quantified. In the context of this disclosure, the effective proximity of the signal molecule and a second molecule element with which it can chemically react or engage in resonant energy transfer, is the distance or range of distance between the signal molecule and the second molecule or element where the interaction can take place such that a measurable change in a signal produced, directly or indirectly, by the signal moiety can be detected and/or quantified.

As used herein, the terms "Fc portion," "Fc region," and the like are used interchangeably herein and refer to the fragment crystallizable region of an antibody that interacts with cell surface receptors called Fc receptors and some proteins of the complement system. The IgG Fc region is composed of two identical protein fragments that are derived from the second and third constant domains of the IgG antibody's two heavy chains.

As used herein, "identity," can refer to a relationship between two or more nucleotide or polypeptide sequences, as determined by comparing the sequences. In the art, "identity" can also refers to the degree of sequence relatedness between polynucleotide or polypeptide sequences as determined by the match between strings of such sequences. "Identity" can be readily calculated by known methods, including, but not limited to, those described in (Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J. Applied Math. 1988, 48: 1073. Preferred methods to determine identity are designed to give the largest match between the sequences tested. Methods to determine identity are codified in publicly available computer programs. The percent identity between two sequences can be determined by using analysis software (e.g., Sequence Analysis Software Package of the Genetics Computer Group, Madison Wis.) that incorporates the Needelman and Wunsch, (J. Mol. Biol., 1970, 48: 443-453) algorithm (e.g., NBLAST, and XBLAST). The default parameters are used to determine the identity for the polypeptides or polynucleotides of the present disclosure, unless stated otherwise.

The term "molecular weight", as used herein, can generally refer to the mass or average mass of a material. If a polymer or oligomer, the molecular weight can refer to the relative average chain length or relative chain mass of the bulk polymer. In practice, the molecular weight of polymers and oligomers can be estimated or characterized in various ways including gel permeation chromatography (GPC) or capillary viscometry. GPC molecular weights are reported as the weight-average molecular weight (Mw) as opposed to the number-average molecular weight (Mn). Capillary viscometry provides estimates of molecular weight as the inherent viscosity determined from a dilute polymer solution using a particular set of concentration, temperature, and solvent conditions.

As used herein, "nucleic acid," "nucleotide sequence," and "polynucleotide" can be used interchangeably herein and can generally refer to a string of at least two base-sugar-phosphate combinations and refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, polynucleotide as used herein can refer to triple-stranded regions comprising RNA or DNA or both RNA and DNA. The strands in such regions can be from the same molecule or from different molecules. The regions may include all of one or more of the molecules, but more typically involve only a region of some of the molecules. One of the molecules of a triple-helical region often is an oligonucleotide. "Polynucleotide" and "nucleic acids" also encompasses such chemically, enzymatically or metabolically modified forms of polynucleotides, as well as the chemical forms of DNA and RNA characteristic of viruses and cells, including simple and complex cells, inter alia. For instance, the term polynucleotide as used herein can include DNAs or RNAs as described herein that contain one or more modified bases. Thus, DNAs or RNAs including unusual bases, such as inosine, or modified bases, such as tritylated bases, to name just two examples, are polynucleotides as the term is used herein. "Polynucleotide", "nucleotide sequences" and "nucleic acids" also includes PNAs (peptide nucleic acids), phosphorothioates, and other variants of the phosphate backbone of native nucleic acids. Natural nucleic acids have a phosphate backbone, artificial nucleic acids can contain other types of backbones, but contain the same bases. Thus, DNAs or RNAs with backbones modified for stability or for other reasons are "nucleic acids" or "polynucleotides" as that term is intended herein. As used herein, "nucleic acid sequence" and "oligonucleotide" also encompasses a nucleic acid and polynucleotide as defined elsewhere herein.

As used herein, the terms "optional" or "optionally" means that the subsequently described event or circumstance can or cannot occur, and that the description includes instances where said event or circumstance occurs and instances where it does not.

As used herein "peptide" can refer to chains of at least 2 amino acids that are short, relative to a protein or polypeptide.

As used herein, "polymer" refers to a chemical compound formed from a plurality of repeating structural units referred to as monomers "Polymers" are understood to include, but are not limited to, homopolymers, copolymers, such as for example, block, graft, random and alternating copolymers, terpolymers, etc. and blends and modifications thereof. Polymers can be formed by a polymerization reaction in which the plurality of structural units become covalently bonded together. When the monomer units forming the polymer all have the same chemical structure, the polymer is a homopolymer. When the polymer includes two or more monomer units having different chemical structures, the polymer is a copolymer.

As used herein, "polypeptides" or "proteins" refers to amino acid residue sequences. Those sequences are written left to right in the direction from the amino to the carboxy terminus.

In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V). "Protein" and "Polypeptide" can refer to a molecule composed of one or more chains of amino acids in a specific order. The term protein is used interchangeable with "polypeptide." The order is determined by the base sequence of nucleotides in the gene coding for the protein. Proteins can be required for the structure, function, and regulation of the body's cells, tissues, and organs.

As used herein, the term "specific binding" can refer to non-covalent physical association of a first and a second moiety wherein the association between the first and second moieties is at least 2 times as strong, at least 5 times as strong as, at least 10 times as strong as, at least 50 times as strong as, at least 100 times as strong as, or stronger than the association of either moiety with most or all other moieties present in the environment in which binding occurs. Binding of two or more entities may be considered specific if the equilibrium dissociation constant, Kd, is $10^{-3}$ M or less, $10^{-4}$ M or less, $10^{-5}$ M or less, $10^{-6}$ M or less, $10^{-7}$ M or less, $10^{-8}$ M or less, $10^{-9}$ M or less, $10^{-10}$ M or less, $10^{-11}$ M or less, or $10^{-12}$ M or less under the conditions employed, e.g., under physiological conditions such as those inside a cell or consistent with cell survival. In some embodiments, specific binding can be accomplished by a plurality of weaker interactions (e.g., a plurality of individual interactions, wherein each individual interaction is characterized by a Kd of greater than $10^{-3}$ M). In some embodiments, specific binding, which can be referred to as "molecular recognition," is a saturable binding interaction between two entities that is dependent on complementary orientation of functional groups on each entity. Examples of specific binding interactions include primer-polynucleotide interaction, aptamer-aptamer target interactions, antibody-antigen interactions, avidin-biotin interactions, ligand-receptor interactions, metal-chelate interactions, hybridization between complementary nucleic acids, etc.

As used herein, "surface," in the context herein, refers to a boundary of a product. The surface can be an interior surface (e.g. the interior boundary of a hollow product), or an exterior or outer boundary or a product. Generally, the surface of a product corresponds to the idealized surface of a three dimensional solid that is topological homeomorphic with the product. The surface can be an exterior surface or an interior surface. An exterior surface forms the outermost layer of a product or device. An interior surface surrounds an inner cavity of a product or device, such as the inner cavity of a tube. As an example, both the outside surface of a tube and the inside surface of a tube are part of the surface of the tube. However, internal surfaces of the product that are not in topological communication with the exterior surface, such as a tube with closed ends, can be excluded as the surface of a product. In some embodiments, an exterior surface of the product is chemically modified, e.g., a surface that can contact a sample component or be coupled to a DNA-nanostructure described herein. In some embodiments, where the product is porous or has holes in its mean (idealized or surface), the internal faces of passages and holes are not considered part of the surface of the product if its opening on the mean surface of the product is less than 1 μm.

As used herein, "substantial" and "substantially," specify an amount of between 95% and 100%, inclusive, between 96% and 100%, inclusive, between 97% and 100%, inclusive, between 98% 100%, inclusive, or between 99% 100%, inclusive.

As used interchangeably herein, "subject," "individual," or "patient" can refer to a vertebrate organism, such as a mammal (e.g. human). "Subject" can also refer to a cell, a population of cells, a tissue, an organ, or an organism, preferably to human and constituents thereof.

As used herein, "substantially free" can mean an object species is present at non-detectable or trace levels so as not to interfere with the properties of a composition or process.

As used herein, "substantially pure" can mean an object species is the predominant species present (i.e., on a molar basis it is more abundant than any other individual species in the composition), and preferably a substantially purified fraction is a composition wherein the object species comprises about 50 percent of all species present. Generally, a substantially pure composition will comprise more than about 80 percent of all species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single species.

As used herein, the term "tethered diffusion" refers to the local diffusion of a moiety that is tethered to a surface, where the moiety is limited from diffusion away from the surface but is diffusing within an approximate hemispherical region of three-dimensional space. In the context of this disclosure, changes in tethered diffusion rates were observed as changes in electrochemical current measured at a nanostructure-modified electrode when anchor molecules were either bound or unbound. Various other modes of measurement (optical, vibrational, etc.) could also be used to report tethered diffusion rates.

As used herein, the terms "weight percent," "wt %," and "wt. %," which can be used interchangeably, indicate the percent by weight of a given component based on the total weight of a composition of which it is a component, unless otherwise specified. That is, unless otherwise specified, all wt % values are based on the total weight of the composition. It should be understood that the sum of wt % values for all components in a disclosed composition or formulation are equal to 100. Alternatively, if the wt % value is based on the total weight of a subset of components in a composition, it should be understood that the sum of wt % values the specified components in the disclosed composition or formulation are equal to 100.

Examples

Figure 2A:
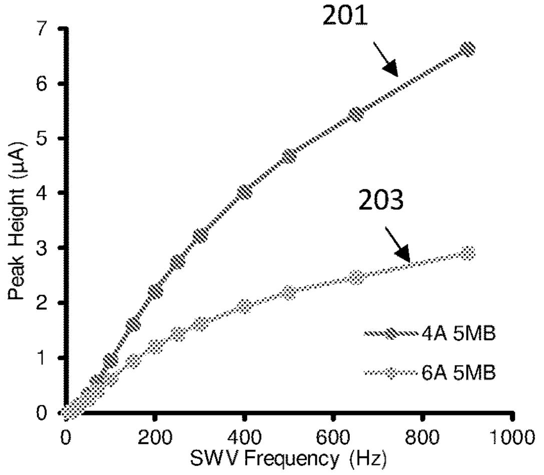
FIG. 2A is a graph showing a comparison of the biotin-conjugated DNA nanostructures with 5 MB tagged signaling DNA at both 4 A and 6 A distances.
Figure 2B:
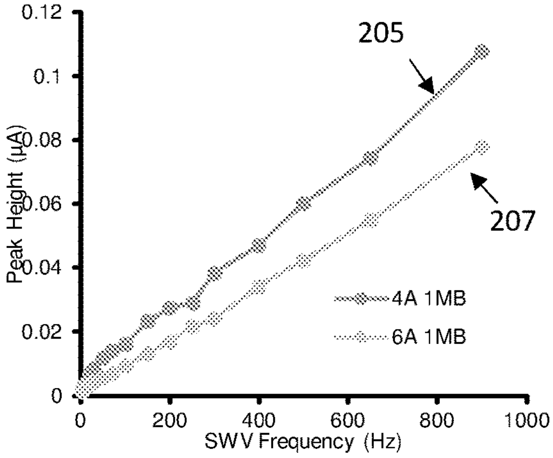
FIG. 2B shows nanostructures with 4 A and 6 A spacers including only a single MB tagged signaling DNA. The initial current signal (peak height in uA) from the 5 MB is ~60× larger than the 1 MB tagged signaling DNA at the same distances at the highest frequency (900 Hz).

In the examples shown and described herein, 1 MB refers to a single methylene blue molecule tagged to the signaling DNA and 5 MB refers to a set of five methylene blue molecules tagged to the equivalent signaling DNA. The graphs/plots shown and described herein may refer to current output from 4-900 Hz for square wave voltammetry frequencies. FIGS. 2A-2B show data from a biotin-conjugated DNA nanostructure while FIGS. 3A-3C, 4A-4B and 5A-5C show data from a tacrolimus-conjugated DNA nanostructure. All data were collected using 2 mm diameter gold-sputtered on glass electrodes.

For example, FIG. 2A shows a signal comparison of a biotin-conjugated DNA nanostructure with 5 MB tagged signaling DNA at both 4 A (201) and 6 A (203) distances. For comparison, FIG. 2B shows a comparison of two biotin-conjugated DNA nanostructures each with 1 MB tagged signaling DNA at 4 A (105) and 6 A (107). Note that the peak heights are significantly higher for the multiple MB-conjugated nanostructures. The initial current signal (peak height in uA) from the 5 MB is ~60× larger than the 1 MB tagged signaling DNA at the same distances at the highest frequency (900 Hz).

Figure 3A:
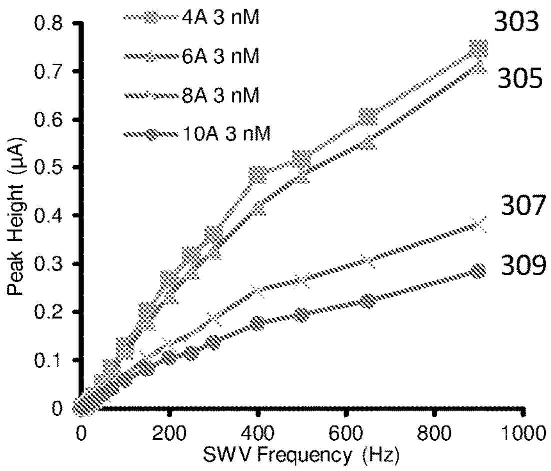
FIGS. 3A-3C are graphs showing initial current signals with different thiol probe density attained by immobilization of various thiol-DNA concentrations, respectively 3 (FIG. 3A), 30 (FIG. 3B), and 300 nM (FIG. 3C). The 3 nM concentration results in lower probe density for each of the 4 A, 6 A, 8 A and 10 A spacings. The 30 nM concentration with moderate probe density for each of the 4 A, 6 A, 8 A and 10 A spacings and the 300 nM included higher probe density. A higher thiol DNA concentration correlates with a higher signal (more nanostructure formations) and an increased distance from the electrode surface correlates with a lower signal (signaling molecule is farther from the electrode surface leading to less electron transfer).
Figure 3B:
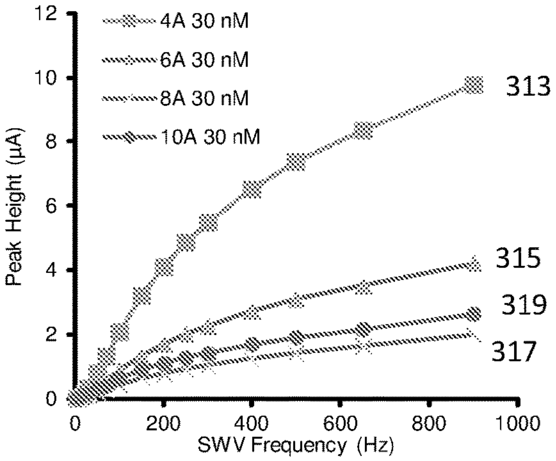
Figure 3C:
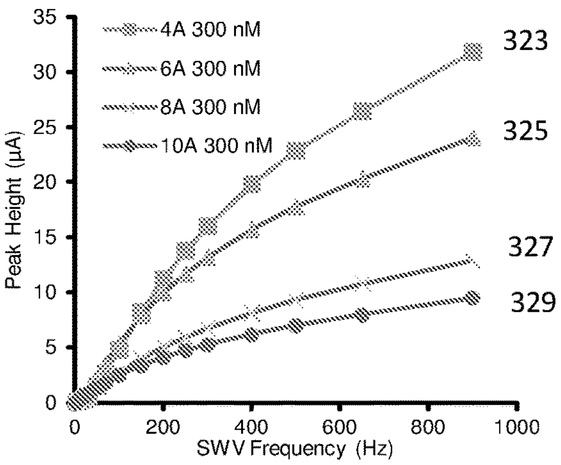

Similarly, the thiol probe density also modifies the signal current. FIGS. 3A-3C show a comparison of initial current signal with different thiol probe density attained by immobilization of various thiol-DNA concentrations (3, 30, 300 nM). FIG. 3A shows a comparison of 4 A (303), 6 A (305), 8 A (307) and 10 A (309) at 3 nM concentrations. In general, 3 nM concentration resulted in lower probe density. For comparison, FIG. 3B shows a comparison of 4 A (313), 6 A (315), 8 A (317) and 10 A (319) at 30 nM showing moderate probe density, FIG. 3C shows a comparison of 4 A (323), 6 A (325), 8 A (327) and 10 A (329) at 300 nM with higher probe density. A higher thiol DNA concentration correlates with a higher signal (more nanostructure formations) and an increased distance from the electrode surface correlates with a lower signal (signaling molecule is farther from the electrode surface leading to less electron transfer).

Figure 4A:
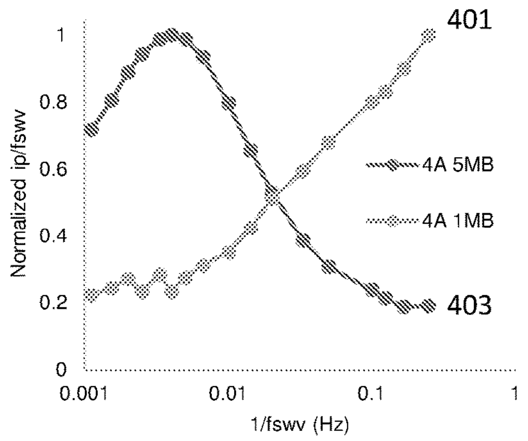
FIGS. 4A-4B are graphs showing critical times of the 5 MB vs. 1 MB tagged DNA at different distances (4 A, 6 A). The 5 MB examples showed a lower critical time so that the probes may interact much more frequently with the electrode surface than the 1 MB at both distances. Having a lower critical time generates a high electrochemical signal and this large initial electrochemical signal and effective shift in the critical time by the anchor help improve the assay sensitivity.
Figure 4B:
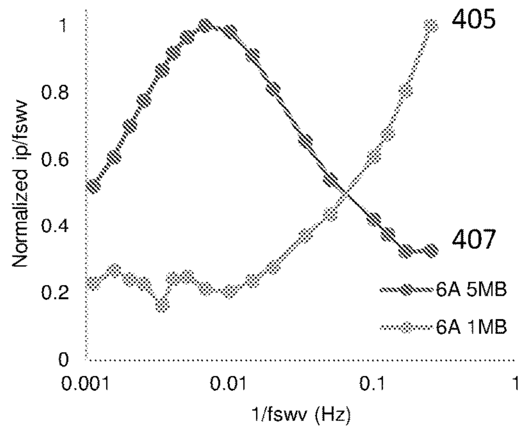

FIGS. 4A-4B compare the critical times of the 5 MB (403, 407) vs. 1 MB (401, 405) tagged DNA at different distances. In FIG. 4A, the distances are 4 A, while in FIG. 4B the distances are 6 A. The lower critical time for 5 MB implies that the probes are interacting much more frequently with the electrode surface than the 1 MB at both distances. Having a lower critical time generates a high electrochemical signal and this large initial electrochemical signal and effective shift in the critical time by the anchor may help improve the assay sensitivity.

Figure 5A:
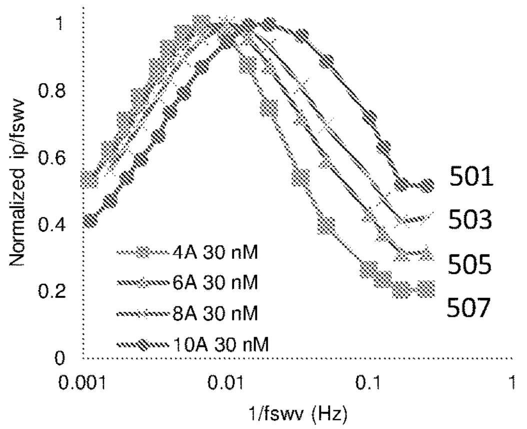
FIGS. 5A-5C show graphs comparing the signal suppression (%) from introducing 100 nM of tacrolimus antibody to the electrode with the DNA nanostructure with different thiol DNA (4 A-10 A).
Figure 5B:
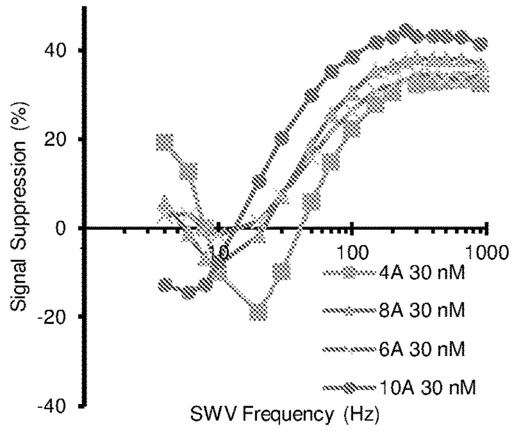
Figure 5C:
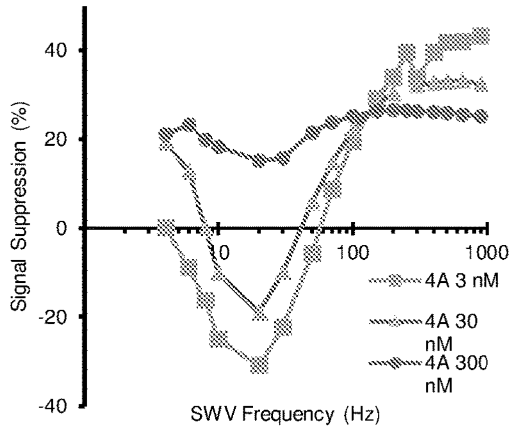

FIG. 5A is a comparison of the critical times of the electrode with the DNA nanostructure with different thiol DNA at 4 A (507), 6 A (505), 8 A (503) and 10 A (501). The critical time increases with an increase in the distance. FIG. 5B illustrates the signal suppression (%) from introducing 100 nM of tacrolimus antibody with a 30 nM thiol DNA concentration, for 4 A, 6 A, 8 A, and 10 A. The 10 A distance has the largest signal suppression tested which is used for correlating with target analyte concentration (e.g. tacrolimus). Similar signal suppression may be found for at least up to 20 A distance. FIG. 5C illustrates signal suppression as inversely correlated with thiol DNA concentration, as a fixed distance of 4 A (517) shows the highest signal suppression at 3 nM thiol DNA concentration (comparison FIGS. 5B and 5C to 5A).

In general, the sensitivity of the assay depends on the signal suppression (e.g., of the antibody or other anchor recognition moiety). Surprisingly, when multiple signal moieties (e.g., multiple MBs) are included, the signal suppression is also modified, and in a manner that changes the spacing dependence of the assay. Previous work (see, e.g., US 20190382764) suggested and taught that the spacing of the signal (e.g., redox) moiety from the substrate should be limited to, preferably about 4 A, and that larger distances should not be used because the signal would be minimal due to this distance dependence, even where larger protein attachments were used. In contrast, the results described herein indicate that when multiple signal moieties (e.g., multiple MBs) are used, the spacing should instead be set to 8 A or greater (e.g., between 8 A and 20 A, more preferably between 10 A and 20 A). This may result in a change in the signal (signal suppression) indicating specific target binding that is significantly greater for spacing between 8 A and 20 A when using multiple (e.g., 3 or more, between 3-10, such as 5) signal moieties including but not limited to MB and other redox moieties. The signal suppression with multiple signal moieties when spaced by between 8 A and 20 A may be greater than 30% (e.g., greater than 35%, 40%, 45%, 50%, etc.). When combined with a concentration of the thiol-DNA spacer that is between 1 nM and 5 uM, the resulting assay is particularly robust and sensitive, in comparison with earlier DNA-nanostructure based assays even using the same signal moieties.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A DNA-based assay comprising:

a continuous DNA molecule comprising a first hairpin structural motif attached to a second hairpin structural motif via a first segment of single stranded DNA;

an anchor recognition moiety coupled to the continuous DNA molecule;

a signal moiety comprising a plurality of redox molecules, wherein the signal moiety is coupled to the continuous DNA molecule, wherein the signal moiety and the anchor recognition moiety are in effective proximity to each other; and a thiol-DNA spacer segment attached at a first end to an electrically conductive substrate and at a second end to the first or second hairpin structural motif such that it forms a single stranded tether region at one end of the single continuous DNA molecule extending between 2.72 and 6.8 nanometers (nm).

2. The assay of claim 1, wherein the signal moiety comprises between 2 and 15 redox molecules.

3. The assay of claim 1, wherein each of the plurality of redox molecule comprises a methylene blue molecule.

4. The assay of claim 1, wherein the concentration of the thiol-DNA spacer is between 1 nM and 5 uM.

5. The assay of claim 1, wherein the signal moiety comprises between 3 and 8 methylene blue molecules and wherein the single stranded tether region extends between 2.04 and 6.8 nm.

6. The system of claim 5, wherein the signal moiety comprises between 4 and 8 redox molecules.

7. The system of claim 5, wherein each of the plurality of redox molecule comprises a methylene blue molecule.

8. The assay of claim 1, wherein the signal moiety comprises between 3 and 8 methylene blue molecules and wherein the single stranded tether region extends between 2.04 and 6.8 nm.

9. The method of claim 8, wherein the signal moiety comprises between 2 and 15 redox molecules.

10. The method of claim 8, wherein each of the plurality of redox molecule comprises a methylene blue molecule.

11. The method of claim 8, where the single stranded tether region extends between 3.4 and 6.8 nm.

12. The method of claim 8, wherein the signal moiety comprises between 3 and 8 methylene blue molecules and wherein the single stranded tether region extends between 3.4 and 6.8 nm.

13. A system comprising:
a nanostructure comprising:
a continuous DNA molecule comprising a first hairpin structural motif attached to a second hairpin structural motif via a first segment of single stranded DNA;
an anchor recognition moiety coupled to the continuous DNA molecule;
a signal moiety comprising between 3 and 10 redox molecules, wherein the signal moiety is coupled to the continuous DNA molecule, wherein the signal moiety and the anchor recognition moiety are in effective proximity to each other; and
a thiol-DNA spacer segment attached at a first end to the first or second hairpin structural motif such that it forms a single stranded tether region at one end of the single continuous DNA molecule extending between 2.72 and 6.8 nanometers (nm); and
an electrode having a surface, wherein the thiol-DNA spacer of the nanostructure is coupled at a second end to the to the surface in a concentration of between 1 nM and 5 uM.

14. A DNA nanostructure-based method, the method comprising:
exposing a DNA-based nanostructure to a sample material comprising a target molecule, wherein the DNA-based nanostructure comprises:
a continuous DNA molecule comprising a first hairpin structural motif attached to a second hairpin structural motif via a first segment of single stranded DNA;
an anchor recognition moiety coupled to the continuous DNA molecule, wherein the anchor recognition moiety binds to the target molecule;
a signal moiety comprising a plurality of redox molecules, wherein the signal moiety is coupled to the continuous DNA molecule,
wherein the signal moiety and the anchor recognition moiety are in effective proximity to each other; and
a thiol-DNA spacer segment attached at a first end to an electrically conductive substrate and at a second end to the first or second hairpin structural motif such that it forms a single stranded tether region at one end of the single continuous DNA molecule extending between 2.72 and 6.8 nanometers (nm); and
quantifying an amount of the target molecule by analyzing the electrochemical signal from the DNA-based nanostructure, wherein the electrochemical signal changes in proportion to changes in concentration of the target.

* * * * *